(12) United States Patent
Yon et al.

(10) Patent No.: US 6,905,494 B2
(45) Date of Patent: Jun. 14, 2005

(54) METHOD AND DEVICE FOR PERFORMING COOLING- OR CRYO-THERAPIES FOR, E.G., ANGIOPLASTY WITH REDUCED RESTENOSIS OR PULMONARY VEIN CELL NECROSIS TO INHIBIT ATRIAL FIBRILLATION EMPLOYING TISSUE PROTECTION

(75) Inventors: Steven A. Yon, San Diego, CA (US); John D. Dobak, III, La Jolla, CA (US); Hans W. Kramer, Temecula, CA (US); Rebecca S. Inderbitzen, San Diego, CA (US)

(73) Assignee: Innercool Therapies, Inc., San Diego, CA (US)

( * ) Notice: Subject to any disclaimer, the term of this patent is extended or adjusted under 35 U.S.C. 154(b) by 6 days.

(21) Appl. No.: 10/086,585

(22) Filed: Feb. 28, 2002

(65) Prior Publication Data

US 2002/0156469 A1 Oct. 24, 2002

Related U.S. Application Data

(63) Continuation-in-part of application No. 09/787,599, filed on Mar. 21, 2001, now Pat. No. 6,602,276, which is a continuation-in-part of application No. 09/516,319, filed on Mar. 1, 2000, which is a continuation-in-part of application No. 09/215,038, filed on Dec. 16, 1998, now Pat. No. 6,261,312, and a continuation-in-part of application No. 09/052,545, filed on Mar. 31, 1998, now Pat. No. 6,231,595, application No. 10/086,585.
(60) Provisional application No. 60/272,550, filed on Mar. 1, 2001, and provisional application No. 60/273,095, filed on Mar. 2, 2001.

(51) Int. Cl.$^7$ ............................................... A61B 18/18
(52) U.S. Cl. .............................. 606/24; 606/20; 606/21; 606/22; 606/23
(58) Field of Search ............................... 606/20–24, 26; 607/105, 106, 113

(56) References Cited

U.S. PATENT DOCUMENTS

| 2,308,484 A | 1/1943 | Auzin et al. |
|---|---|---|
| 2,374,609 A | 4/1945 | McCollum |
| 2,615,686 A | 10/1952 | Davidson |

(Continued)

FOREIGN PATENT DOCUMENTS

| AU | 730835 B2 | 8/1997 |
|---|---|---|
| AU | 685559 B2 | 1/1998 |
| AU | 743945 B2 | 8/1998 |

(Continued)

OTHER PUBLICATIONS

Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.

(Continued)

*Primary Examiner*—Rosiland Rollins
(74) *Attorney, Agent, or Firm*—Mayer Fortkort & Williams PC; Mark Wieczorek, Esq.; Karin L. Williams, Esq.

(57) ABSTRACT

An enhanced method and device are provided to treat atrial fibrillation or inhibit or reduce restenosis following angioplasty or stent placement. A balloon-tipped catheter is disposed in the area treated or opened through balloon angioplasty immediately following angioplasty. The balloon, which can have a dual balloon structure, may be delivered through a guiding catheter and over a guidewire already in place. A fluid such as a perfluorocarbon flows into the balloon to freeze the tissue adjacent the balloon, this cooling being associated with reduction of restenosis. A similar catheter may be used to reduce atrial fibrillation by inserting and inflating the balloon such that an exterior surface of the balloon contacts at least a partial circumference of the portion of the pulmonary vein adjacent the left atrium. In another embodiment, blood perfusion is performed simultaneously. In another embodiment, tissue contacted by the cryoablation catheter, undesired to be ablated, is protected against damage by a separate heating step.

15 Claims, 12 Drawing Sheets

U.S. PATENT DOCUMENTS

| | | | |
|---|---|---|---|
| 2,672,032 A | 3/1954 | Towse |
| 2,913,009 A | 11/1959 | Kuthe |
| 3,125,096 A | 3/1964 | Antiles et al. |
| 3,228,400 A | 1/1966 | Armao |
| 3,298,371 A | 1/1967 | Lee |
| 3,369,549 A | 2/1968 | Armao |
| 3,425,419 A | 2/1969 | Dato |
| 3,504,674 A | 4/1970 | Swenson et al. |
| 3,612,175 A | 10/1971 | Ford et al. |
| 3,674,031 A | 7/1972 | Weiche |
| 3,696,813 A | 10/1972 | Wallach |
| 3,786,814 A | 1/1974 | Armao |
| 3,859,986 A | 1/1975 | Okada et al. |
| 3,865,116 A | 2/1975 | Brooks |
| 3,867,294 A | 2/1975 | Pall et al. |
| 3,888,259 A | 6/1975 | Miley |
| 3,889,680 A | 6/1975 | Armao |
| 3,948,269 A * | 4/1976 | Zimmer | 606/24 |
| 3,971,383 A | 7/1976 | van Gerven |
| 4,038,519 A | 7/1977 | Foucras |
| 4,153,048 A | 5/1979 | Magrini |
| 4,190,033 A | 2/1980 | Foti |
| 4,231,425 A | 11/1980 | Engstrom |
| 4,275,734 A | 6/1981 | Mitchiner |
| 4,298,006 A | 11/1981 | Parks |
| 4,318,722 A | 3/1982 | Altman |
| 4,323,071 A | 4/1982 | Simpson et al. |
| 4,348,873 A | 9/1982 | Yamauchi et al. |
| 4,427,009 A | 1/1984 | Wells et al. |
| 4,445,500 A | 5/1984 | Osterholm |
| 4,483,341 A | 11/1984 | Witteles |
| 4,502,286 A | 3/1985 | Okada et al. |
| 4,569,355 A | 2/1986 | Bitterly |
| 4,581,017 A | 4/1986 | Sahota |
| 4,602,642 A | 7/1986 | O'Hara |
| 4,655,746 A | 4/1987 | Daniels et al. |
| 4,672,962 A | 6/1987 | Hershenson |
| 4,745,922 A | 5/1988 | Taylor |
| 4,747,826 A | 5/1988 | Sassano |
| 4,748,979 A | 6/1988 | Hershenson |
| 4,750,493 A | 6/1988 | Brader |
| 4,762,130 A | 8/1988 | Fogarty et al. |
| 4,781,033 A | 11/1988 | Steyert |
| 4,781,799 A | 11/1988 | Herbert, Jr. et al. |
| 4,860,744 A | 8/1989 | Johnson et al. |
| 4,883,455 A | 11/1989 | Leonard |
| 4,894,164 A | 1/1990 | Polaschegg |
| 4,904,237 A | 2/1990 | Janese |
| 4,920,963 A | 5/1990 | Brader |
| 4,946,460 A * | 8/1990 | Merry et al. | 606/24 |
| 4,951,677 A | 8/1990 | Crowley et al. |
| 4,964,409 A | 10/1990 | Tremulis |
| 5,000,734 A | 3/1991 | Boussignac et al. |
| 5,014,695 A | 5/1991 | Benak et al. |
| 5,018,521 A | 5/1991 | Campbell |
| 5,019,075 A | 5/1991 | Spears et al. |
| 5,024,668 A | 6/1991 | Peters et al. |
| 5,041,089 A | 8/1991 | Mueller et al. |
| 5,046,497 A | 9/1991 | Millar |
| 5,078,713 A | 1/1992 | Varney |
| 5,089,260 A | 2/1992 | Hunter et al. |
| 5,092,841 A | 3/1992 | Spears |
| 5,106,360 A | 4/1992 | Ishwara et al. |
| 5,106,368 A | 4/1992 | Uldall et al. |
| 5,108,390 A | 4/1992 | Potocky et al. |
| 5,110,721 A | 5/1992 | Anaise et al. |
| 5,112,438 A | 5/1992 | Bowers |
| 5,117,822 A | 6/1992 | Laghi |
| 5,147,355 A | 9/1992 | Friedman et al. |
| 5,149,321 A | 9/1992 | Klatz et al. |
| 5,150,706 A | 9/1992 | Cox et al. |
| 5,151,100 A | 9/1992 | Abele et al. |
| 5,180,364 A | 1/1993 | Ginsburg |
| 5,190,539 A | 3/1993 | Fletcher et al. |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,264,260 A | 11/1993 | Saab |
| 5,267,341 A | 11/1993 | Shearin |
| 5,269,369 A | 12/1993 | Faghri |
| 5,269,749 A | 12/1993 | Koturov |
| 5,269,758 A | 12/1993 | Taheri |
| 5,281,213 A | 1/1994 | Milder et al. |
| 5,281,215 A | 1/1994 | Milder |
| 5,306,261 A | 4/1994 | Alliger et al. |
| 5,310,440 A | 5/1994 | Zingher |
| 5,334,193 A | 8/1994 | Nardella |
| 5,342,301 A | 8/1994 | Saab |
| 5,344,436 A | 9/1994 | Fontenot et al. |
| 5,365,750 A | 11/1994 | Greenthal |
| 5,368,591 A | 11/1994 | Lennox et al. |
| 5,383,854 A | 1/1995 | Safar et al. |
| 5,383,918 A | 1/1995 | Panetta |
| 5,395,314 A | 3/1995 | Klatz et al. |
| 5,395,331 A | 3/1995 | O'Neill et al. |
| 5,403,281 A | 4/1995 | O'Neill et al. |
| 5,417,686 A | 5/1995 | Peterson et al. |
| 5,423,745 A | 6/1995 | Todd et al. |
| 5,423,807 A | 6/1995 | Milder |
| 5,433,740 A | 7/1995 | Yamaguchi |
| 5,437,673 A | 8/1995 | Baust et al. |
| 5,462,521 A | 10/1995 | Brucker et al. |
| 5,486,204 A | 1/1996 | Clifton |
| 5,486,208 A | 1/1996 | Ginsburg |
| 5,496,271 A | 3/1996 | Burton et al. |
| 5,531,776 A | 7/1996 | Ward et al. |
| 5,549,559 A | 8/1996 | Eshel |
| 5,554,119 A | 9/1996 | Harrison et al. |
| 5,558,644 A | 9/1996 | Boyd et al. |
| 5,573,532 A | 11/1996 | Chang et al. |
| 5,578,008 A | 11/1996 | Hara |
| 5,584,804 A | 12/1996 | Klatz et al. |
| 5,588,438 A | 12/1996 | McKown et al. |
| 5,591,162 A | 1/1997 | Fletcher et al. |
| 5,620,480 A | 4/1997 | Rudie |
| 5,622,182 A | 4/1997 | Jaffe |
| 5,624,392 A | 4/1997 | Saab |
| 5,630,837 A | 5/1997 | Crowley |
| 5,647,051 A | 7/1997 | Neer |
| 5,653,692 A | 8/1997 | Masterson et al. |
| 5,709,654 A | 1/1998 | Klatz et al. |
| 5,713,941 A | 2/1998 | Robins et al. |
| 5,716,386 A | 2/1998 | Ward et al. |
| 5,733,280 A | 3/1998 | Avitall |
| 5,733,318 A | 3/1998 | Augustine |
| 5,735,809 A | 4/1998 | Gorsuch |
| 5,741,248 A | 4/1998 | Stern et al. |
| 5,797,878 A | 8/1998 | Bleam |
| 5,799,661 A | 9/1998 | Boyd et al. |
| 5,800,480 A | 9/1998 | Augustine et al. |
| 5,800,483 A | 9/1998 | Vought |
| 5,800,488 A | 9/1998 | Crockett |
| 5,800,516 A | 9/1998 | Fine et al. |
| 5,807,391 A | 9/1998 | Wijkamp |
| 5,820,593 A | 10/1998 | Safar et al. |
| 5,824,030 A | 10/1998 | Yang et al. |
| 5,827,222 A | 10/1998 | Klatz et al. |

| | | |
|---|---|---|
| 5,827,237 A | 10/1998 | Macoviak et al. |
| 5,827,269 A | 10/1998 | Saadat |
| 5,833,671 A | 11/1998 | Macoviak et al. |
| 5,837,003 A | 11/1998 | Ginsburg |
| 5,861,021 A | 1/1999 | Thome |
| 5,868,735 A | 2/1999 | Lafontaine |
| 5,871,526 A | 2/1999 | Gibbs et al. |
| 5,873,835 A | 2/1999 | Hastings et al. |
| 5,879,316 A | 3/1999 | Safar et al. |
| 5,879,329 A | 3/1999 | Ginsburg |
| 5,899,899 A | 5/1999 | Arless et al. |
| 5,901,783 A | 5/1999 | Dobak, III et al. |
| 5,902,268 A | 5/1999 | Saab |
| 5,906,588 A | 5/1999 | Safar et al. |
| 5,906,594 A | 5/1999 | Scarfone et al. |
| 5,906,636 A | 5/1999 | Casscells, III et al. |
| 5,913,856 A | 6/1999 | Chia et al. |
| 5,913,885 A | 6/1999 | Klatz et al. |
| 5,913,886 A | 6/1999 | Soloman |
| 5,916,242 A | 6/1999 | Schwartz |
| 5,957,917 A | 9/1999 | Doiron et al. |
| 5,964,751 A | 10/1999 | Amplatz et al. |
| 5,967,976 A | 10/1999 | Larsen et al. |
| 5,968,009 A | 10/1999 | Simán |
| 5,971,979 A | 10/1999 | Joye et al. |
| 5,989,238 A | 11/1999 | Ginsburg |
| 5,992,158 A | 11/1999 | Goddard et al. |
| 6,007,692 A | 12/1999 | Herbert et al. |
| 6,012,457 A | 1/2000 | Lesh |
| 6,019,783 A | 2/2000 | Philips et al. |
| 6,022,336 A | 2/2000 | Zadno-Azizi et al. |
| 6,024,740 A | 2/2000 | Lesh et al. |
| 6,033,383 A | 3/2000 | Ginsburg |
| 6,063,101 A | 5/2000 | Jacobsen et al. |
| 6,110,168 A | 8/2000 | Ginsburg |
| 6,126,684 A | 10/2000 | Gobin et al. |
| 6,146,411 A | 11/2000 | Noda et al. |
| 6,146,814 A | 11/2000 | Millet |
| 6,149,670 A | 11/2000 | Worthen et al. |
| 6,149,673 A | 11/2000 | Ginsburg |
| 6,149,676 A | 11/2000 | Ginsburg |
| 6,149,677 A | 11/2000 | Dobak, III |
| 6,152,144 A | 11/2000 | Lesh et al. |
| 6,165,207 A | 12/2000 | Balding et al. |
| 6,168,594 B1 | 1/2001 | Lafontaine et al. |
| 6,182,666 B1 | 2/2001 | Dobak, III |
| 6,193,644 B1 | 2/2001 | Dobak, III et al. |
| 6,213,126 B1 | 4/2001 | Lafontaine et al. |
| 6,217,528 B1 | 4/2001 | Koblish et al. |
| 6,224,624 B1 | 5/2001 | Lasheras et al. |
| 6,231,561 B1 | 5/2001 | Frazier et al. |
| 6,231,594 B1 | 5/2001 | Dae |
| 6,231,595 B1 | 5/2001 | Dobak, III |
| 6,235,018 B1 | 5/2001 | LePivert |
| 6,235,019 B1 | 5/2001 | Lehmann et al. |
| 6,235,048 B1 | 5/2001 | Dobak, III |
| 6,238,428 B1 | 5/2001 | Werneth et al. |
| 6,241,722 B1 | 6/2001 | Dobak et al. |
| 6,245,095 B1 | 6/2001 | Dobak, III et al. |
| 6,248,057 B1 | 6/2001 | Mavity et al. |
| 6,251,093 B1 | 6/2001 | Valley et al. |
| 6,251,129 B1 | 6/2001 | Dobak, III et al. |
| 6,251,130 B1 | 6/2001 | Dobak, III et al. |
| 6,253,769 B1 | 7/2001 | LaFontaine et al. |
| 6,254,588 B1 | 7/2001 | Jones et al. |
| 6,254,626 B1 | 7/2001 | Dobak, III et al. |
| 6,261,312 B1 | 7/2001 | Dobak, III et al. |
| 6,264,679 B1 | 7/2001 | Keller et al. |
| 6,267,747 B1 | 7/2001 | Samson et al. |
| 6,270,476 B1 | 8/2001 | Santoianni et al. |
| 6,270,493 B1 | 8/2001 | Lalonde et al. |
| 6,270,494 B1 | 8/2001 | Kovalcheck et al. |
| 6,287,326 B1 | 9/2001 | Pecor |
| 6,290,674 B1 | 9/2001 | Roue et al. |
| 6,290,696 B1 | 9/2001 | LaFontaine |
| 6,290,697 B1 | 9/2001 | Tu et al. |
| 6,290,717 B1 | 9/2001 | Phillips |
| 6,295,990 B1 | 10/2001 | Lewis et al. |
| 6,296,654 B1 | 10/2001 | Ward |
| 6,299,599 B1 | 10/2001 | Pham |
| 6,305,378 B1 | 10/2001 | Lesh |
| 6,306,161 B1 | 10/2001 | Ginsburg |
| 6,312,452 B1 | 11/2001 | Dobak, III et al. |
| 6,325,818 B1 | 12/2001 | Werneth |
| 6,338,727 B1 | 1/2002 | Noda et al. |
| 6,364,899 B1 | 4/2002 | Dobak, III |
| 6,368,304 B1 | 4/2002 | Aliberto et al. |
| 6,383,151 B1 | 5/2002 | Diederich et al. |
| 6,383,180 B1 | 5/2002 | Lalonde et al. |
| 6,391,224 B1 | 5/2002 | Wowk |
| 6,393,320 B2 | 5/2002 | Lasersohn et al. |
| 6,423,018 B1 | 7/2002 | Augustine |
| 6,461,379 B1 | 10/2002 | Carson et al. |
| 6,497,720 B1 | 12/2002 | Augustine et al. |
| 6,595,989 B1 * | 7/2003 | Schaer ........................ 606/41 |
| 2001/0001830 A1 | 5/2001 | Dobak, III et al. |
| 2001/0001831 A1 | 5/2001 | Dobak, III et al. |
| 2001/0001832 A1 | 5/2001 | Dobak, III et al. |
| 2001/0002442 A1 | 5/2001 | Dobak, III |
| 2001/0005791 A1 | 6/2001 | Ginsburg et al. |
| 2001/0007927 A1 | 7/2001 | Koblish et al. |
| 2001/0007951 A1 | 7/2001 | Dobak, III |
| 2001/0008975 A1 | 7/2001 | Dobak, III et al. |
| 2001/0010011 A1 | 7/2001 | Aliberto et al. |
| 2001/0011184 A1 | 8/2001 | Dobak, III et al. |
| 2001/0011185 A1 | 8/2001 | Dobak, III et al. |
| 2001/0014802 A1 | 8/2001 | Tu |
| 2001/0016763 A1 | 8/2001 | Lasheras et al. |
| 2001/0016764 A1 | 8/2001 | Dobak, III |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0031946 A1 | 10/2001 | Walker et al. |
| 2001/0032004 A1 | 10/2001 | Werneth |
| 2001/0039440 A1 | 11/2001 | Lasheras et al. |
| 2001/0041923 A1 | 11/2001 | Dobak, III |
| 2001/0044644 A1 | 11/2001 | Keller et al. |
| 2001/0047191 A1 | 11/2001 | Lasersohn et al. |
| 2001/0047192 A1 | 11/2001 | Lasersohn et al. |
| 2001/0047196 A1 | 11/2001 | Ginsburg et al. |
| 2001/0049545 A1 | 12/2001 | Lasersohn et al. |
| 2002/0002394 A1 | 1/2002 | Dobak, III |
| 2002/0007179 A1 | 1/2002 | Dobak, III et al. |
| 2002/0007202 A1 | 1/2002 | Dobak, III et al. |
| 2002/0007203 A1 | 1/2002 | Gilmartin et al. |
| 2002/0007206 A1 | 1/2002 | Bui et al. |
| 2002/0016621 A1 | 2/2002 | Werneth et al. |
| 2002/0022823 A1 | 2/2002 | Luo et al. |
| 2002/0026227 A1 | 2/2002 | Philips |
| 2002/0029016 A1 | 3/2002 | Pham et al. |
| 2002/0032430 A1 | 3/2002 | Luo et al. |
| 2002/0032438 A1 | 3/2002 | Lafontaine |
| 2002/0032474 A1 | 3/2002 | Dobak, III et al. |
| 2002/0049409 A1 | 4/2002 | Noda et al. |
| 2002/0049410 A1 | 4/2002 | Noda et al. |
| 2002/0087095 A1 | 7/2002 | Burbank et al. |

FOREIGN PATENT DOCUMENTS

| | | |
|---|---|---|
| AU | 737433 B2 | 2/1999 |
| AU | 739996 B2 | 8/1999 |
| AU | 734506 C | 10/1999 |
| CA | 2177982 A | 6/1995 |

| | | |
|---|---|---|
| CN | 1082382 A | 2/1994 |
| EP | 0655225 A1 | 5/1993 |
| EP | 0 664 990 | 11/1997 |
| FR | 2 447 406 | 3/1980 |
| SU | 806 029 | 2/1981 |
| WO | WO 91/05528 | 5/1991 |
| WO | WO 93/04727 | 3/1993 |
| WO | WO 94/16760 | 8/1994 |
| WO | WO 95/01814 | 1/1995 |
| WO | WO 95/15115 | 6/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 98/38934 | 9/1998 |
| WO | WO 98/49957 | 11/1998 |
| WO | WO 99/02096 | 1/1999 |
| WO | WO 99/04211 | 1/1999 |
| WO | WO 99/27862 | 6/1999 |
| WO | WO 99/44519 | 10/1999 |
| WO | WO 99/56812 | 11/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/62837 | 10/2000 |
| WO | WO 00/66053 | 11/2000 |
| WO | WO 00/72779 | 12/2000 |
| WO | WO 00/72787 | 12/2000 |
| WO | WO 01/03606 | 1/2001 |
| WO | WO 01/08580 | 2/2001 |
| WO | WO 01/10323 | 2/2001 |
| WO | WO 01/10365 | 2/2001 |
| WO | WO 01/12061 | 2/2001 |
| WO | WO 01/12122 | 2/2001 |
| WO | WO 01/13837 | 3/2001 |
| WO | WO 01/17471 | 3/2001 |
| WO | WO 01/19447 | 3/2001 |
| WO | WO 01/26590 | 4/2001 |
| WO | WO 01/30413 | 5/2001 |
| WO | WO 01/34225 | 5/2001 |
| WO | WO 01/37919 | 5/2001 |
| WO | WO 01/41664 | 6/2001 |
| WO | WO 01/41708 | 6/2001 |
| WO | WO 01/43661 | 6/2001 |
| WO | WO 01/49236 | 7/2001 |
| WO | WO 01/52781 | 7/2001 |
| WO | WO 01/54618 | 8/2001 |
| WO | WO 01/54764 | 8/2001 |
| WO | WO 01/56517 | 8/2001 |
| WO | WO 01/58397 | 8/2001 |
| WO | WO 01/64145 | 9/2001 |
| WO | WO 01/64146 | 9/2001 |
| WO | WO 01/66052 | 9/2001 |
| WO | WO 01/74276 | 10/2001 |
| WO | WO 01/76655 | 10/2001 |
| WO | WO 01/78580 | 10/2001 |
| WO | WO 01/87379 | 11/2001 |
| WO | WO 01/95840 | 12/2001 |
| WO | WO 02/00128 | 1/2002 |
| WO | WO 02/13710 | 2/2002 |

OTHER PUBLICATIONS

Arless, S. G., *CryoCath Completes a Third Round Private Placement for CDN$10 Million*, Apr. 7, 1999, Kirkland, Quebec, Press Release.

Arless, S. G., *CryoCath Technologies, Inc.*, Oct. 1999, press release.

Asbach, H. W. et al., *The Effects of Extreme Cold on Major Blood Vessels; An Experimental Study* (abs.), Urologe A., May 1975, vol. 14, No. 3, pp. 150–153.

Atrionix (Palo Alto, CA), *AF Ablation and Monitoring*, http://www.medicaldata.com/members/MPM/3–2000/0300–3.asp, Apr. 19, 2000.

Bigelo; *Hypothermia, Its Possible Role in Cardiac Surgery*; Nov. 1959; pp. 849–866; Annals of Surgery, vol. 132, No. 5.

Bokeriia, A. A. et al., *Cryogenic Effect on the coronary Arteries in Animal Experiments* (abs.), Biull. Eksp.Biol. Med., Jun. 1988, vol. 105, Nov. 6, pp. 741–743.

Cheatle; *Cryostripping the Long and Short Saphenous Veins*; Jan. 1993; one page; Br. J. Surg., vol. 80.

Colvett, K. T. et al. "Opportunities with Combined Modality Therapy for Selective Organ Preservation in Muscle–Invasive Bladder Cancer," May 1996, *Journ. Surg. Oncology* 63:202–201.

CryoCath Technologies Inc.: The hottest new technology in ablation is cold, press brochure, Kirkland, Quebec, Canada.

CryoCath Technologies, Inc., *Affairs of the Heart*, The Gazette, Montreal, Feb. 16, 1998.

Dexter; *Blood Warms as It Flows Retrograde from a Femoral Cannulation Site to the Carotid Artery During Cardiopulmonary Bypass*; Nov. 1994; pp. 393–397; Perfusion, vol. 9, No. 6.

Dorval, J–F et al. *Induction of Extracellular Matrix Expression in the Arterial Wall after the Application of Cryotherapy in a Porcine PTCA Model*, ACC Meeting, Mar. 2000, No. 1131–116.

Dubuc, M. et al. *Catheter Cryoablation: A Novel Technology for Ablation of Cardiac Arrhythmias*, presented at AHA, Nov. 1996.

Dubuc, M. et al. *Feasibility of Cardiac Cryoablation Using a Transvenous Steerable Electrode Catheter*, reprint Journal of Interventional Electrophysiology, vol. 2, No. 3, Kluwer Academic Publishers, 1998, vol. 2, pp. 285–292.

Dubuc, M. et al. *Reversible Electrophysiologic Effects Using Ice Mapping with a Cryoablation Catheter*, Montreal, Quebec, Canada, Brigham and Women's Hospital, Boston, MA, presented at NSPE, May 1997.

Dubuc, M. et al. *Transvenous Catheter Ice Mapping and Cryoablation of the Atrioventricular Node in Dogs*, Oct. 1999, P.A.C.E., vol. 22, No. 10, pp. 1488–1498.

Ducharme, A. et al. *Intracardiac Echocardiography Monitoring of Catheter Cryoablation*, presented at AHA, Nov. 1998.

Gillinov; *Superior Cerebral Protection with Profound Hypothermia During Circulatory Arrest*; Nov. 1992; pp. 1432–1439; Ann. Thorac. Surg., vol. 55.

Haines, N. S., *Biophysics and Pathology of Catheter Energy Delivery Systems* (abs.), Prog. Cardiovasc. Dis., Jan.–Feb. 1995, vol. 37, No. 4, pp. 185–204.

Hayes, N. S., "Temperature control in extracorporeal circulation," Aug. 17, 1968, *Brit. Med. J. 2(615):430*.

Higazi; *The Effect of Ultrasonic Irradiation and Temperature on Fibrinolytic Activity in Vitro*; Aug. 1992; p. 251–253; Thrombosis Research, vol. 69, No. 2.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

Jos, R.C. Jansen, Ph.D., et al. (1997) *Near Continuous Cardiac Output by Thermodilution.* Journal of Clinical Monitoring 13:233–239.

Keane, D. et al. *Percutaneous Cryothermal Catheter Ablation for the Creation of Linear Atrial Lesions*, Massachusetts General Hospital, Boston, MA, presented at NASPE, May 1999.

Kimoto; *Open Heart Surgery under Direct Vision with the Aid of Brain–Cooling by Irrigation*; Jul. 1955; pp. 592–603, Surgery, vol. 39, No. 4.

Ladd, A. P. et al. *Cryosurgical Effects on Growing Vessels* (abs.), Am Surg. Jul. 1999, vol. 65, No. 7, pp. 677–682.

Lustgarten, D. L. et al. (1999), *Cryothermal Ablation: Mechanism of Tissue Injury and Current Experience in the Treatment of Tachyarrhythmias*, 47(6):481–498.

Marekovic, Z.; *Abstract of Renal Hypothermia in Situ by Venous Passages: Experimental Work on Dogs*; 1980; Eur Urol 6(2); 1 page.

Marsland, A. R. et al., *Cryogenic Damage to Peripheral Nerves and Blood Vessels in the Rat*, Br. J. Anaesth., Jun. 1983, vol. 55, No. 6, pp. 555–558.

Mass, C. et al. "Intermittent Antegrade/Selective Cerebral Perfusion during Circulatory Arrest for Repair of the Aortic Arch," 1997, *Perfusion, 12*:127–132.

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stroke Model*; Feb. 1994; pp. 131–138; Brain Research, vol. 647.

Milleret, Rene; *La cryo–chirurgie danes les varices des mimbres inferieurs*; Angiologie; Supplement au No. 110.

Milleret; Abstract of *Cryosclerosis of the Saphenous Veins in Varicose Reflux in the Obese and Elderly*; 10.1981; one/page Phlebologie, vol. 34, No. 4.

Parkins; *Brain Cooling in the Prevention of Brain Damage During Periods of Circulatory Occlusion in Dogs*; Apr. 1954; pp. 284–289; Annals of Surgery, vol. 140, No. 3.

Pham, I. et al., *Adenovirus Mediated Atrial Natriuretic Peptide Gene Transfer in Rat Pulmonary Vascular Smooth Muscle Cells Leads to Inhibition of Cell Growth and Apoptosis*, Section on: Therapeutic Strategies in Vascular Remodeling, AHA Meeting, Nov. 1998, Dallas, Texas, No. 3544.

Piepgras; *Rapid Active Internal Core Cooling for Induction of Moderate Hypothermia in Head Injury by Use of an Extracorporeal Heat Exchanger*; Feb. 1998; pp. 311–318; Neurosurgery, vol. 42, No. 2.

Plattner, O. et al. *Efficacy of Intraoperative Cooling Methods*, 1997, Anesthesiology, Nov., vol. 87, No. 5, pp. 1089–1095.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Schwartz, A. E. et al.; (1996); *Isolated cerebral hypothermia by single carotid artery perfusion of extracorporeally cooled blood in baboons*; Neurosurgery 39(3):577–582.

Schwartz; *Cerebral Blood Flow during Low–flow Hypothermic Cardiopulmonary Bypass in Baboons*; Jun. 1994; pp. 959–964; Anesthesiology, vol. 81, No. 4.

Schwartz; *Selective Cerebral Hypothermia by Means of Transfemoral Internal Carotid Artery Catheterization*; May 1996; pp. 571–572; Radiology, vol. 201, No. 2.

Steen; *The Detrimental Effects of Prolonged Hypothermia and Rewarming in the Dog*; Aug. 1979 ;pp. 224–230; Anesthesiology, vol. 52, No. 3.

Tanguay, J.–F., *A New Cryotherapy Catheter to Prevent Restenosis* (abs.), $11^{th}$ Transcatheter Cardiovascular Therapeutics, Sep. 1999.

Tanguay, J–F et al. *A New Cryocatheter Treatment Improves Vascular Remodeling after Angioplasty*, presented at AHA, Nov. 1998.

Tanguay, J–F et al.,*A New Cryocatheter Treatment Improves Vascular Remodeling after Angioplasty*, Section on Therapeutic Strategies in Vascular Remodeling, AHA Meeting, Nov. 1998, Dallas, Texas, No. 3543.

Vandam; *Hypothermia*; Sep. 1959; pp. 546–553; The New England Journal of Medicine.

White; *Cerebral Hypothermia and Circulatory Arrest*, Jul. 1978; pp. 450–458; Mayo Clinic Proceedings, vol. 53.

Yenari; *Thrombolysis with Tissue Plasminogen Activator (TPA) is Temperature Dependent*; Jul. 1994; pp. 475–481; Thrombosis Research, vol. 77, No. 5.

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, No. 2.

* cited by examiner

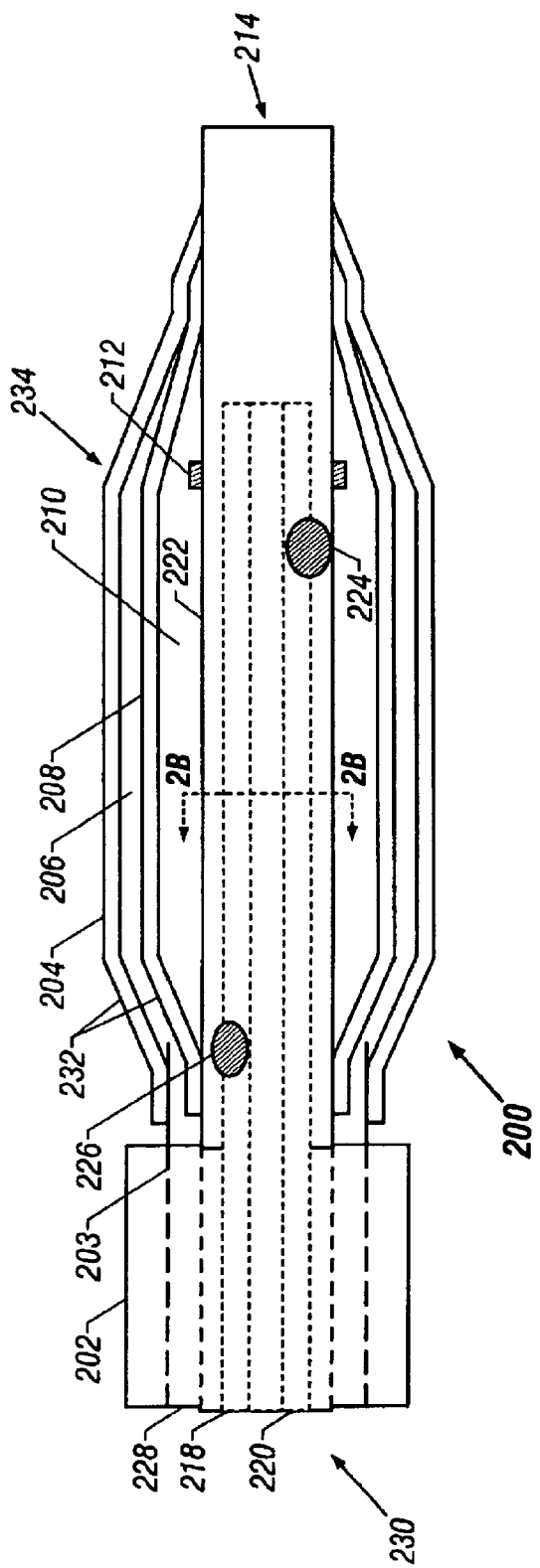
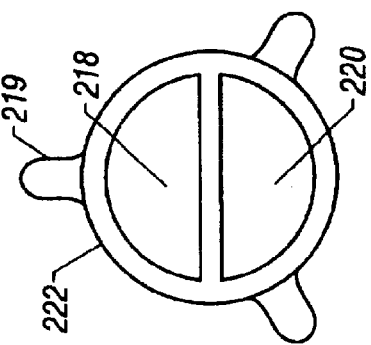
FIG. 2A
FIG. 2B

METHOD AND DEVICE FOR PERFORMING COOLING- OR CRYO-THERAPIES FOR, E.G., ANGIOPLASTY WITH REDUCED RESTENOSIS OR PULMONARY VEIN CELL NECROSIS TO INHIBIT ATRIAL FIBRILLATION EMPLOYING TISSUE PROTECTION

CROSS-REFERENCE TO RELATED APPLICATIONS

This application is a continuation-in-part of U.S. patent application Ser. No. 09/787,599 filed Mar. 21, 2001, now U.S. Pat. No. 6,602,276 entitled "Method and Device for Performing Cooling-or Cryo-Therapies for, e.g., Angioplasty with Reduced Restenosis or Pulmonary Vein Cell Necrosis to Inhibit Atrial Fibrillation" which is a continuation-in-part of U.S. patent application Ser. No. 09/516,319, filed Mar. 1, 2000 entitled "Method and Device for Performing Cooling-or Cryo-Therapies for, e.g., Angioplasty with Reduced Restenosis or Pulmonary Vein Cell Necrosis to Inhibit Atrial Fibrillation" which is a continuation-in-part of U.S. patent application Ser. No. 09/052,545, filed Mar. 31, 1998, now U.S. Pat. No. 6,231,595 entitled "Circulating Fluid Hypothermia Method and Apparatus" and U.S. patent application Ser. No. 09/215,038, filed Dec. 16, 1998, now U.S. Pat. No. 6,261,312 entitled "Inflatable Catheter for Selective Organ Heating and Cooling and Method of Using the Same". This application is also continuation-in-part and utility conversion of Provisional Application Ser. Nos.: 60/272,550 filed Mar. 1, 2001, entitled "Method and Apparatus for Inhibiting Tissue Damage During Cryo-Ablation", and 60/273,095 filed Mar. 2, 2001, entitled "Annular Ring Balloon for Pulmonary Vein Cryoplasty", all of the above are incorporated herein.

CROSS-REFERENCE TO MICROFICHE APPENDIX (None)

BACKGROUND OF THE INVENTION

Balloon angioplasty, or the technology of reshaping of a blood vessel for the purpose of establishing vessel patency using a balloon tipped catheter, has been known since the late 1970's. The procedure involves the use of a balloon catheter that is guided by means of a guidewire through a guiding catheter to the target lesion or vessel blockage. The balloon typically is equipped with one or more marker bands that allow the interventionalist to visualize the position of the balloon in reference to the lesion with the aid of fluoroscopy. Once in place, i.e., centered with the lesion, the balloon is inflated with a biocompatible fluid, and pressurized to the appropriate pressure to allow the vessel to open.

Typical procedures are completed with balloon inflation pressures between 8 and 12 atmospheres. A percentage of lesions, typically heavily calcified lesions, require much higher balloon inflation pressures, e.g., upward of 20 atmospheres. At times, the balloon inflation procedure is repeated several times before the lesion or blockage will yield. The placement of stents after angioplasty has become popular as it reduces the rate of restenosis.

Restenosis refers to the renarrowing of the vascular lumen following vascular intervention such as a balloon angioplasty procedure or stent insertion. Restenosis is clinically defined as a greater than 50% loss of initial lumen diameter. The mechanism or root causes of restenosis are still not fully understood. The causes are multifactorial, and are partly the result of the injury caused by the balloon angioplasty procedure and stent placement. With the advent of stents, restenosis rates have dropped from over 30% to 10–20%. Recently, the use and effectiveness of low-dose radiation administered intravascularly following angioplasty is being evaluated as a method to alter the DNA or RNA of an affected vessel's cells in the hope of reducing cell proliferation.

Another cardiological malady is atrial fibrillation. Atrial fibrillation is common following various cardiac surgeries, e.g., valve surgery. Atrial fibrillation refers to very rapid irregular contractions of the atria of the heart resulting in a lack of synchronization between the heartbeat and the pulse. The irregular contractions are due to irregular electrical activity that originates in the area of the pulmonary veins. A proposed device, currently under development, for treating atrial fibrillation is a balloon filled with saline that can be ultrasonically agitated and heated. This device is inserted in the femoral vein and snaked into the right atrium. The device is then poked through the interatrial septum and into the left atrium, where it is then angled into the volume adjoining the suspect pulmonary vein with the left atrium.

Research in atrial fibrillation indicates that substantially complete circumferential necrosis is required for a therapeutic benefit. The above technique is disadvantageous in that circumferential portions of the tissue, desired to be necrosed, are not in fact affected. Other techniques, including RF ablation, are similarly inefficient. Moreover, these techniques leave the necrosed portions with jagged edges, i.e., there is poor demarcation between the healthy and the necrosed tissue. These edges can then cause electrical short circuits, and associated electrical irregularities, due to the high electric fields associated with jagged edges of a conductive medium.

The above technique is also disadvantageous in that heating is employed. Heating is associated with several problems, including increased coagulum and thrombus formation, leading to emboli. Heating also stimulates stenosis of the vein. Finally, since tissues can only safely be heated to temperatures of less than or about 75° C.–85° C. due to charring and tissue rupture secondary to steam formation. The thermal gradient thus induced is fairly minimal, leading to a limited heat transfer. Moreover, since heating causes tissues to become less adherent to the adjacent heat transfer element, the tissue contact with the heat transfer element is also reduced, further decreasing the heat transfer.

Another disadvantage that may arise during either cooling or heating results from the imperfections of the surface of the tissue at or adjacent to the point of contact with the cryoballoon (in the case of cooling). In particular, surface features of the tissue may affect the local geometry such that portions of the balloon attain a better contact, and thus a better conductive heat transfer, with the tissue. Such portions may be more likely to achieve cell necrosis than other portions. As noted above, incomplete circumferential necrosis is often deleterious in treating atrial fibrillation and may well be further deleterious due to the necessity of future treatments. Accordingly, a method and device to achieve better conductive heat transfer between tissue to be ablated and an ablation balloon is needed.

A further disadvantage with prior systems arises from the temperature of the components. In particular, it is preferable if only the atrial tissue is exposed to cryogenic temperatures. However, occasionally, other tissues is exposed, such as the tissue at or near the insertion site of the catheter. Thermal tissue damage may occasionally occur.

In some situations, pulmonary vein cryo-ablation for treatment of atrial fibrillation may require long occlusion times, such as greater than five minutes. In such situations, there is a risk of stroke, which is clearly a disadvantageous result.

Prior attempts to remedy this included a perfusion balloon that facilitated flow through the catheter shaft. This design suffered from various drawbacks, such as the necessity of bringing the blood into deleteriously close contact with the refrigerant, and the insufficiency of space to provide unrestricted blood flow through the catheter. In another prior approach, a helical or star-shaped balloon was used which was self-centering. This design also suffered from various drawbacks, such as unequal ablation around the circumference.

SUMMARY OF THE INVENTION

The present invention provides an enhanced method and device to treat atrial fibrillation or to inhibit or reduce the rate of restenosis following angioplasty or stent placement. The invention is similar to placing an ice pack on a sore or overstrained muscle for a period of time to minimize or inhibit the biochemical events responsible for an associated inflammatory response. An embodiment of the invention generally involves placing a balloon-tipped catheter in the area treated or opened through balloon angioplasty immediately following angioplasty. A so-called "cryoplasty" balloon, which can have a dual balloon structure, may be delivered through a guiding catheter and over a guidewire already in place from a balloon angioplasty. The dual balloon structure has benefits described below and also allows for a more robust design. The balloon is porous so that an amount of ablation fluid is delivered to the tissue at the ablation site.

The balloon may be centered in the recently opened vessel with the aid of radio opaque marker bands, indicating the "working length" of the balloon. In choosing a working length, it is important to note that typical lesions may have a size on the order of 2–3 cm. In the dual balloon design, biocompatible heat transfer fluid, which may contain contrast media, may be infused through the space between the dual balloons. While this fluid does not circulate in this embodiment, once it is chilled or even frozen by thermal contact with a cooling fluid, it will stay sufficiently cold for therapeutic purposes. Subsequently, a biocompatible cooling fluid with a temperature between about, e.g., −40° C. and −60° C., may be injected into the interior of the inner balloon, and circulated through a supply lumen and a return lumen. The fluid exits the supply lumen through a skive in the lumen, and returns to the refrigeration unit via another skive and the return lumen.

The biocompatible cooling fluid chills the biocompatible heat transfer fluid between the dual balloons to a therapeutic temperature between about, e.g., 0° C. and −50° C. The chilled heat transfer fluid between the dual balloons transfers thermal energy through the balloon wall and into the adjacent intimal vascular tissue for the appropriate therapeutic length of time.

To aid in conduction, a small portion of the chilled heat transfer fluid between the dual balloons may contact the adjacent intimal vascular tissue for the appropriate therapeutic length of time due to the porosity or microporosity of the outer balloon.

Upon completion of the therapy, the circulation of the biocompatible cooling fluid is stopped, and the remaining heat transfer fluid between the dual balloons withdrawn through the annular space. Both balloons may be collapsed by means of causing a soft vacuum in the lumens. Once collapsed, the cryoplasty catheter may be withdrawn from the treated site and patient through the guiding catheter.

The device may further include a source of chilled fluid having a supply tube and a return tube, the supply tube coupled in fluid communication to the supply lumen and the return tube coupled in fluid communication to the return lumen. The source of fluid may be coupled in fluid communication to a volume between the inner balloon and the outer balloon. The fluid may be a perfluorocarbon such as Galden fluid. The fluid may also include contrast media.

In one aspect, the invention is directed towards a device and method to mitigate blood flow stasis during application of cryoablation therapies. Perfusion during cryoablation minimizes the risk of embolization of a clot, leading to stroke or myocardial infarction, and further minimizes the freezing of blood.

In yet another aspect, the invention may be used in a prophylactic sense, i.e., may be employed following cardiac surgeries, such as valve surgery, to prevent a case of atrial fibrillation that might otherwise occur.

In yet another aspect, the invention is directed towards a device and method to limit tissue damage at, e.g., the site of insertion into the patient's body, the atrial septum, and so on. Embodiments of the device may include a source of warmed fluid at circulates at or adjacent the site of insertion, a resistive heater employed at or adjacent the site of insertion, or other similar devices.

In a further aspect, the invention is directed to a device to treat tissue while preventing tissue damage to adjacent tissue, including an ablation catheter; an introducer sheath for the ablation catheter, the introducer sheath at least partially contacting tissue to be protected; and a heater disposed adjacent or within the introducer sheath, the heater thermally coupled to the tissue; and a control unit for the heater.

Variations of the invention may include one or more of the following. The heater may be a resistive heater or may include an inlet tube fluidically coupled to an interior of the introducer and at least one outlet orifice disposed in the introducer. The heater may include an inlet sleeve with an input for a body fluid at a distal end of the introducer sheath, where the inlet sleeve is fluidically coupled to an interior of the introducer, and at least one outlet orifice disposed in the introducer. The inlet sleeve may have an annular shape along a portion thereof. The resistive heater may be disposed on a sleeve, the sleeve concentric with the introducer sheath, and may be helically wound on the sleeve. The ablation catheter may further define a guidewire lumen; a supply lumen; and a return lumen. The guidewire lumen may extend from a proximal end of the ablation catheter to a distal end of the ablation catheter. The device may further include a marker band disposed on the ablation catheter to locate a working region of the device at a desired location. The device may further include a source of cryo-ablation fluid having a supply tube and a return tube, the supply tube coupled in fluid communication to the supply lumen and the return tube coupled in fluid communication to the return lumen. The cryo-ablation fluid, also called a cryofluid or a working fluid, may be a perfluorocarbon, Galden® fluid, DMSO, d-limonene, or the like. The source of the working fluid may include a gear pump for circulating the cryofluid, where the gear pump may be a radial spur gear pump, a helical tooth gear pump, or the like.

In yet a further aspect, the invention is directed to a method of treating atrial fibrillation while preventing tissue damage to the atrial septum, including: inserting a trocar wire capable of rupturing the atrial septum from the femoral vein into the right atrium; forming a hole using the trocar wire in the atrial septum between the right atrium and the left atrium; inserting an introducer sheath into the hole, the introducer sheath at least partially contacting the atrial septum; inserting a guide wire through the introducer sheath into the right atrium and left atrium and further into a pulmonary vein; disposing an ablation catheter over the guidewire into a volume defined by the joint of the left atrium and the pulmonary vein; flowing a cryofluid into a balloon disposed within the ablation catheter to ablate tissue adjacent the joint of the left atrium and the pulmonary vein; and operating and controlling a heater disposed adjacent or within the introducer sheath, the heater thermally coupled to the atrial septum.

Variations of the method may include one or more of the following. The operating and controlling a heater including providing power to a resistive heater, or flowing a warming fluid into an inlet tube fluidically coupled to an interior of the introducer sheath, and flowing the warming fluid out of at least one outlet orifice disposed in the introducer sheath. The operating and controlling a heater may also include allowing a body fluid to flow in an inlet sleeve having an input for the body fluid at a distal end of the introducer sheath, wherein the inlet sleeve may be fluidically coupled to an interior of the introducer, and allowing the body fluid to flow out of the at least one outlet orifice disposed in the introducer.

In another aspect, the invention is directed to a method of performing a cryosurgery while preventing tissue damage to the point of insertion, including: percutaneously forming an insertion hole in a vessel of a patient; inserting an introducer sheath into the insertion hole, the introducer sheath at least partially contacting tissue at the insertion hole; inserting a cryogenic catheter through the introducer sheath; disposing the cryogenic catheter at a predefined location; flowing a cryogenic liquid into the cryogenic catheter; and operating and controlling a heater disposed adjacent or within the introducer sheath, the heater thermally coupled to the tissue at the insertion hole.

In a further aspect, the invention is directed to a method of reducing atrial fibrillation, including: inserting a catheter at least partially into the heart, the catheter having a cold balloon, a portion of the balloon located in the left atrium and a portion of the balloon located in a pulmonary vein; and inflating the cold balloon with a working fluid including d-limonene or DMSO such that an exterior surface of the cold balloon may be in contact with at least a partial circumference of the portion of the pulmonary vein adjacent the left atrium, the working fluid having a temperature in the range of about −10° C. to −100° C.

In yet a further aspect, the invention is directed towards a method of reducing restenosis after angioplasty in a blood vessel, including: inserting a catheter into a blood vessel, the catheter having a balloon; and inflating the balloon with a working fluid including DSMO or d-limonene such that an exterior surface of the balloon may be in contact with at least a partial inner perimeter of the blood vessel, the working fluid having a temperature in the range of about −10° C. to −100° C.

In another aspect, the invention is directed towards a device to perform a cryo-ablation treatment while allowing blood perfusion, including: a catheter shaft having a supply lumen and a return lumen; an annular ring balloon fluidically coupled to the catheter shaft, the annular ring balloon having a fluid inlet coupled to the supply lumen, and a fluid outlet coupled to the return lumen, the fluid inlet displaced relative to the fluid outlet, a plane of the annular ring balloon substantially normal to the catheter shaft when inflated; and a source of working fluid, the source having an inlet coupled to the return lumen and an outlet coupled to the supply lumen.

Variations of the device may include one or more of the following. The fluid inlet may be displaced in a proximal direction relative to the fluid outlet. The source of working fluid may include a gear pump.

In a further aspect, the invention is directed to a device to perform a cryo-ablation treatment while allowing blood perfusion, including: a catheter shaft having a catheter supply lumen and a catheter return lumen; an annular ring balloon fluidically coupled to the catheter shaft, the annular ring balloon having a balloon supply lumen coupled to the catheter supply lumen, and a balloon return lumen coupled to the catheter return lumen, an inlet for the balloon supply lumen displaced relative to an outlet of the balloon return lumen, a plane of the annular ring balloon substantially normal to the catheter shaft when inflated; and a source of working fluid, the source having an inlet coupled to the catheter return lumen and an outlet coupled to the catheter supply lumen.

In yet a further aspect, the invention is directed to a method of reducing atrial fibrillation, including: inserting a catheter at least partially into the heart, the catheter having an annular ring balloon disposed near a distal portion thereof, a portion of the annular ring balloon located in the left atrium and a portion of the annular ring balloon located in a pulmonary vein; and inflating the annular ring balloon with a working fluid such that an exterior surface of the annular ring balloon may be in contact with at least a partial circumference of the portion of the pulmonary vein adjacent the left atrium, the working fluid having a temperature in the range of about −10° C. to −100° C.

Advantages of the invention may include one or more of the following. The invention inhibits or reduces the rate of restenosis following a balloon angioplasty or any other type of vascular intervention. At least the following portions of the vascular anatomy can benefit from such a procedure: the abdominal aorta (following a stent or graft placement), the coronary arteries (following PTCA or rotational artherectomy), the carotid arteries (following an angioplasty or stent placement), as well as the larger peripheral arteries.

When the invention is used to treat atrial fibrillation, the following advantages inure. The cooled tissue is adherent to the heat transfer element and/or to the ablative fluid, increasing the heat transfer effected. Since very cold temperatures may be employed, the temperature gradient can be quite large, increasing the heat transfer rate. The ablative fluid that passes from the balloon to the tissue may assist the heat transfer conduction and the ensuing cell necrosis.

In both embodiments, heat transfer does not occur primarily or at all by vaporization of a liquid, thus eliminating a potential cause of bubbles in the body. Nor does cooling occur primarily or at all by a pressure change across a restriction or orifice, this simplifying the structure of the device. Thrombus formation and charring, associated with prior techniques, are minimized or eliminated.

Tissue, undesired to be ablated, may be subject to a separate heating step or element in order to prevent the same from exposure to the cryoablative fluid.

Additional advantages will be apparent from the description that follows, including the drawings and claims.

BRIEF DESCRIPTION OF THE DRAWINGS

FIG. 2A shows a side schematic view of a catheter according to a second embodiment of the invention.

FIG. 2B shows a cross-sectional view of the catheter of FIG. 2A, as indicated by lines 2B—2B in FIG. 2A.

DETAILED DESCRIPTION

Figure 1A:
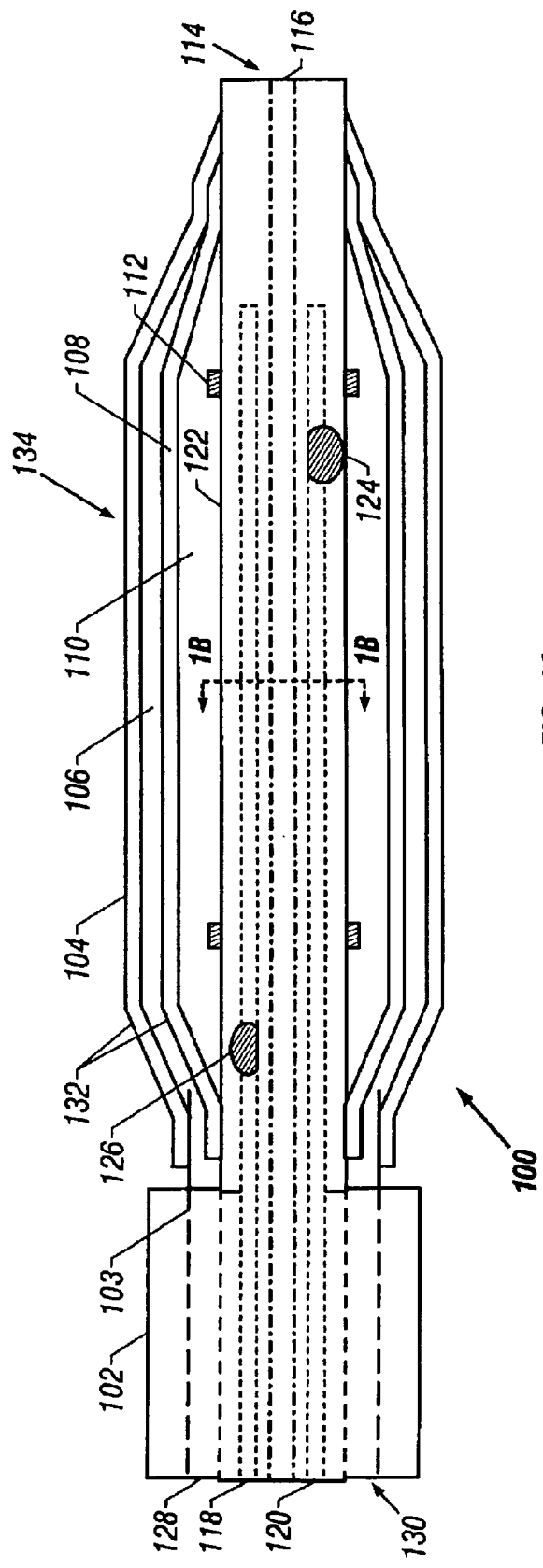
FIG. 1A shows a side schematic view of a catheter according to a first embodiment of the invention.

Referring to FIG. 1A, a catheter 100 is shown according to a first embodiment of the invention. The catheter 100 has a proximal end 130 and a distal end 114. Of course, this figure is not necessarily to scale and in general use the proximal end 130 is far upstream of the features shown in FIG. 1A.

The catheter 100 may be used within a guide catheter 102, and generally includes an outer tube 103, a dual balloon 134, and an inner tube 122. These parts will be discussed in turn.

The guide catheter 102 provides a tool to dispose the catheter 100 adjacent the desired location for, e.g., angioplasty or reduction of atrial fibrillation. Typical guide catheter diameters may be about 6 French to 9 French, and the same may be made of polyether blockamide, polyamides, polyurethanes, and other similar materials. The distal end of the guide catheter is generally adjacent the proximal end of the dual balloon 134, and further is generally adjacent the distal end of the outer tube 103.

The ability to place the guide catheter is a significant factor in the size of the device. For example, to perform angioplasty in the carotid arteries, which have an inner diameter of about 4 to 6 mm, a suitably sized guide catheter must be used. This restricts the size of the catheter 100 that may be disposed within the guide catheter. A typical diameter of the catheter 100 may then be about 7 French or less or about 65 to 91 mils. In a second embodiment described below, a catheter for use in the coronary arteries is described. Of course, which catheter is used in which artery is a matter to be determined by the physician, taking into account such factors as the size of the individual patient's affected arteries, etc.

The outer tube 103 houses the catheter 100 while the latter traverses the length of the guide catheter 102. The outer tube 103 may have a diameter of about 4 French to 7 French, and the same may be made of polyether blockamide, polybutylene terephtalate, polyurethane, polyamide, polyacetal polysulfone, polyethylene, ethylene tetrafluoroethylene, and other similar materials.

The distal end of the outer tube 103 adjoins the proximal end of the dual balloon 134. The outer tube 103 provides a convenient location for mounting a proximal end of an outer balloon 104 within the dual balloon 134, and further may provide an inlet 128 for providing a fluid such as a liquid to a first interior volume 106 between the dual balloons. In some cases, an inlet 128 per se may not be necessary: the fluid, which may also be a sub-atmospheric level of gas or air, may be provided during manufacture in the first interior volume 106. In this case, the proximal and distal ends of the first interior volume may be sealed during manufacture. The inlet 128 may be at least partially defined by the annular volume between the interior of the outer tube 103 and the exterior of the inner tube 122.

The dual balloon 134 includes an outer balloon 104 and an inner balloon 108. Between the two is the first interior volume 106. The outer balloon 104 may be inflated by inflating the interior volume 106. The inner balloon 108 has a second interior volume 110 associated with the same. The inner balloon 108 may be inflated by inflating the second interior volume 110.

To avoid the occurrence of bubbles in the bloodstream, both the inner balloon 108 and the outer balloon 104 may be inflated using biocompatible liquids, such as Galden® fluid, perfluorocarbon-based liquids, or various contrast agents. Fluids such as DMSO, d-limonene, and the like may also be employed. There is no need that the fluid inflating one of the interior volumes be the same fluid as that inflating the other. Additional details on these fluids are described below.

In the case of the first interior volume 106, this fluid may be, e.g., stationary or static: in other words, it need not be circulated. In the case of the second interior volume 110, this fluid would in general be circulated by an external chiller (not shown). The chiller may be, e.g., a gear pump, peristaltic pump, etc. It may be preferable to use a gear pump over a peristaltic pump as the attainable pressure of the former is generally greater than that of the latter. Moreover, gear pumps have the advantageous property of being linear, i.e., their output varies in direction proportion with their revolutions per minute. Two types of gear pumps which may be employed include radial spur gear pumps and helical tooth gear pumps. Of these, the helical tooth gear pump may be more preferable as the same has been associated with higher pressures and a more constant output. The ability to achieve high pressures may be important as the cooling fluid is required to pass through a fairly narrow, e.g., five to seven French, catheter at a certain rate. For the same reason, the viscosity of the fluid, at the low temperatures, should be appropriately low. In this way, e.g., the flow may be increased. For example, an appropriate type of fluid may be Galden® fluid, and in particular Galden® fluid item number "HT-55", available from Ausimont Inc. of Thorofare, N.J. At −55° C., this fluid has a viscosity of 2.1 centiStokes. At −70° C., this fluid has a viscosity of 3.8 centiStokes. It is believed that fluids with such viscosities at these temperatures would be appropriate for use.

The so-called "cones" of the balloons 108 and 104, indicated generally by reference numeral 132, may be made somewhat thicker than the remainder of the balloon sections. In this way, the heat transfer efficiency in these sections is significantly less than over the remainder of the balloon sections, this "remainder" effectively defining a "working region" of the balloon. In this way, the cooling or "cryoplasty" may be efficiently localized to the affected area rather than spread over the length of the balloon.

Figure 1C:
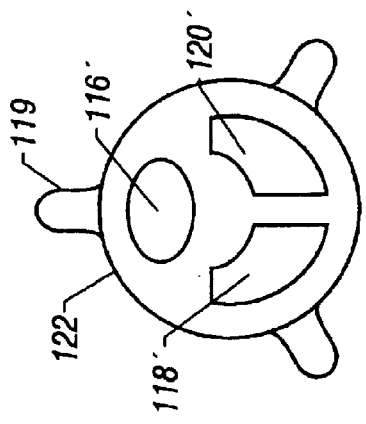
FIG. 1C shows an alternate cross-sectional view of the catheter of FIG. 1A, as indicated by lines 1B—1B in FIG. 1A.
Figure 1B:
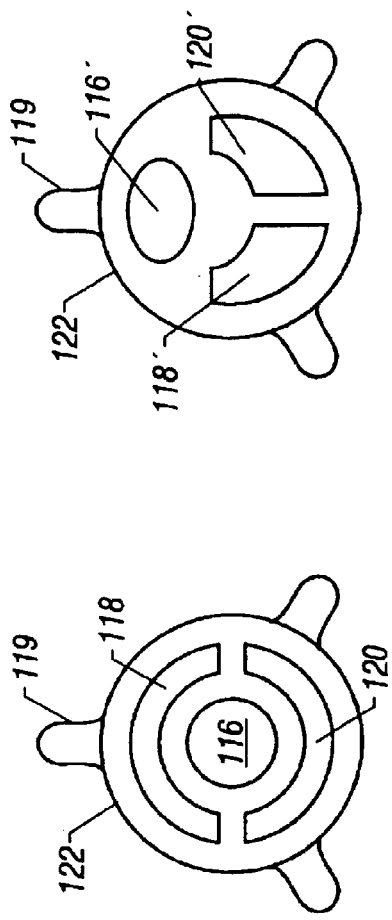
FIG. 1B shows a cross-sectional view of the catheter of FIG. 1A, as indicated by lines 1B—1B in FIG. 1A.

The inner tube 122 is disposed within the interior of the dual balloon 134 and within the interior of the guide catheter 102. The inner tube 122 includes a supply lumen 120, a return lumen 118, and a guidewire lumen 116. The guidewire lumen 116 may have sizes of, e.g., 17 or 21 mils inner diameter, in order to accommodate current standard sized guidewires, such as those having an outer diameter of 14 mils. This structure may be preferable, as the pressure drop encountered may be substantially less. In use, the supply lumen 120 may be used to supply a circulating liquid to the second interior volume 110. The return lumen 118 may be used to exhaust the circulating liquid from the second interior volume to the external chiller. As may be seen from FIG. 1A, both lumens 118 and 120 may terminate prior to the distal end 114 of the catheter 100. The lumen arrangement may be seen more clearly in FIG. 1B. FIG. 1C shows an alternate such arrangement, and one that may provide an even better design for minimal pressure drop. In this design, lumens 118' and 120' are asymmetric about guidewire lumen 116'.

A set of radio opaque marker bands 112 may be disposed on the inner tube 122 at locations substantially adjacent the cones 132 to define a central portion of the "working region" of the balloons 104 and 108. This working region is where the "cryoplasty" procedures described below may substantially occur.

As noted above, the proximal portion of the outer balloon 104 is mounted on the outer tube 103 at its distal end. The distal end of the outer balloon 104 is secured to the distal end of the catheter 100 and along the inner tube 122. In contrast, both the proximal and distal ends of the inner balloon 108 may be secured to the inner tube 122 to create a sealed second interior volume 110.

At least two skives 124 and 126 may be defined by the inner tube 122 and employed to allow the working fluid to exit into the second interior volume 110 and to exhaust the same from the second interior volume 10. As shown in the figure, the skive 124 is in fluid communication with the lumen 120 and the skive 126 is in fluid communication with the lumen 118. Here, "fluid communication" refers to a relationship between two vessels where a fluid pressure may cause a net amount of fluid to flow from one vessel to the other.

The skives may be formed by known techniques. A suitable size for the skives may be from about 50 mils to 125 mils.

A plurality of optional tabs 119 may be employed to roughly or substantially center the inner tube 122 within the catheter 100. These tabs may have the shape shown, the shape of rectangular or triangular solids, or other such shapes so long as the flow of working fluid is not unduly impeded. In this specification, the phrase "the flow of working fluid is not unduly impeded" is essentially equated to the phrase "substantially center". The tabs 119 may be made of polyether blockamide, poly-butylene terephtalate, polyurethane, polyamide, polyacetal polysulfone, polyethylene, ethylene tetrafluoroethylene, and other similar materials, and may have general dimensions of from about 3 mils to 10 mils in height, and by about 10 mils to 20 mils in width.

In a method of use, the guide catheter 102 may be inserted into an affected artery or vein such that the distal tip of the guide catheter is just proximal to an affected area such as a calcified area or lesion. Of course, it is noted that typical lesions do not occur in the venous system, but only in the arterial.

This step provides a coarse estimate of proper positioning, and may include the use of fluoroscopy. The guide catheter may be placed using a guide wire (not shown). Both the guide catheter and guide wire may already be in place as it may be presumed a balloon angioplasty or stent placement has previously been performed.

The catheter 100 may then be inserted over the guide wire via the lumen 116 and through the guide catheter 102. In general, both a guide wire and a guide catheter are not strictly necessary—one or the other may often suffice. During insertion, the dual balloon 134 may be uninflated to maintain a minimum profile. In fact, a slight vacuum may be drawn to further decrease the size of the dual balloon 134 so long as the structural integrity of the dual balloon 134 is not thereby compromised.

When the catheter 100 is distal of the distal tip of the guide catheter 102, a fine positioning step may occur by way of the radio opaque marker bands 112. Using fluoroscopy, the location of the radio opaque marker bands 112 can be identified in relation to the location of the lesion. In particular, the catheter may be advantageously placed at the location of the lesion and further such that the lesion is between the two marker bands. In this way, the working region of the balloon 134 will substantially overlap the affected area, i.e., the area of the lesion.

Once placed, a biocompatible heat transfer fluid, which may also contain contrast media, may be infused into the first interior volume 106 through the inlet 128. While the use of contrast media is not required, its use may allow early detection of a break in the balloon 104 because the contrast media may be seen via fluoroscopy to flow throughout the patient's vasculature. Subsequently a biocompatible cooling fluid may be circulated through the supply lumen 120 and the return lumen 118. Before or during the procedure, the temperature of the biocompatible cooling fluid may be lowered to a therapeutic temperature, e.g., between −40° C. and −60° C., although the exact temperature required depends on the nature of the affected area. The fluid exits the supply lumen 120 through the skive 124 and returns to the chiller through the skive 126 and via the return lumen 118.

It is understood that the respective skive functions may also be reversed without departing from the scope of the invention.

The biocompatible cooling fluid in the second interior volume 110 chills the biocompatible heat transfer fluid within the first interior volume 106 to a therapeutic temperature of, e.g., between about −25° C. and −50° C. The chilled heat transfer fluid transfers thermal energy through the wall of the balloon 104 and into the adjacent intimal vascular tissue for an appropriate therapeutic length of time. This time may be, e.g., about ½ to 4 minutes.

Upon completion of the therapy, the circulation of the biocompatible cooling fluid may cease. The heat transfer fluid within the first interior volume 106 may be withdrawn though the inlet 128. The balloons 104 and 108 may be collapsed by pulling a soft vacuum through any or all of the lumens 124, 126, and 128. Following collapse, the catheter 100 may be withdrawn from the treatment site and from the patient through the guide catheter 102.

To inhibit restenosis, the following therapeutic guidelines may be suggested:

|  | Minimum | Average | Maximum |
| --- | --- | --- | --- |
| Temperature of heat transfer fluid | −20° C. | −55° C. | −110° C. |
| Temperature achieved at intimal wall | 0° C. to −10° C. | −20° C. to −30° C. | −50° C. to −100° C. |
| Depth of penetration of intema/media | 10ths of mm | 1 mm | 3 mm |
| Length of time fluid is circulating | 30 seconds | 1–2 min | 4–5 min |

Substantially the same catheter may be used to treat atrial fibrillation. In this method, the catheter is inflated as above once it is in location. The location chosen for treatment of atrial fibrillation is such that the working region spans a portion of the left atrium and a portion of the affected pulmonary vein. Thus, in this embodiment, the working region of the catheter may have a length of about 5 mm to 30 mm. The affected pulmonary vein, of the four possible pulmonary veins, which enter the left atrium, may be determined by electrophysiology studies.

To maneuver the catheter into this location, a catheter with a needle point may first be inserted at the femoral vein and routed up to the right atrium. The needle of the catheter may then be poked through the interatrial septum and into the left atrium. The catheter may then be removed if desired and a guide catheter disposed in the same location. A guide wire may be used through the guide catheter and may be maneuvered at least partially into the pulmonary vein. Finally, a catheter such as the catheter 100 may be placed in the volume defining the intersection of the pulmonary vein and the left atrium.

A method of use similar to that disclosed above is then employed to cool at least a portion of, and preferably all of, the circumferential tissue. The coldness of the balloon assists in the adherence of the circumferential tissue to the balloon, this feature serving to increase the overall heat transfer rate.

The catheter 100 above may be particularly useful for procedures in the carotid arteries by virtue of its size. For use in the coronary arteries, which are typically much smaller than the carotid artery, an even smaller catheter may be desired. For example, one with an outer diameter less than 5 French may be desired.

Referring to FIG. 2A, a catheter 200 is shown according to a second embodiment of the invention. This embodiment may be particularly useful for use in the coronary arteries because the dimensions of the catheter 200 may be considerably smaller than the dimensions of the catheter 100. However, in several ways the catheter 200 is similar to the above-described catheter 100. In particular, the catheter 200 has a proximal end 230 and a distal end 214 and may be used within a guide catheter 202. The catheter 200 includes an outer tube 203, a dual balloon 234, and an inner tube 222.

The ability to place the guide catheter is a significant factor in the size of the device. For example, to perform angioplasty in the coronary arteries, which have an inner diameter of about 1½ to 4½ mm, a suitably sized guide catheter may be used. This then restricts the size of the catheter 200 which may be disposed within the guide catheter. A typical diameter of the catheter 200 may then be about 3 French or less or about 35–39 mils. The same may be placed in the femoral artery in order to be able to track to the coronary arteries in a known manner.

Analogous to these features in the catheter 100, the outer tube 203 houses the catheter 200 and may have an outside diameter of about 5 French to 7 French, and the same may be made of similar materials. The distal end of the outer tube 203 adjoins the proximal end of the dual balloon 234. The outer tube 203 provides a mounting location for an outer balloon 204, and further provides an inlet 228 for providing a fluid such as a liquid to a first interior volume 206 between the dual balloons. As noted in connection with catheter 100, an inlet 228 per se may not be necessary: the fluid, which may also be a sub-atmospheric level of air, may be provided in the first interior volume 206. Also as above, the proximal and distal ends of the volume may be sealed during manufacture. The inlet 228 may be at least partially defined by the annular volume between the interior of the outer tube 203 and the exterior of the inner tube 222.

The dual balloon 234 includes an outer balloon 204 and an inner balloon 208. These balloons are basically similar to balloons 104 and 108 described above, but may be made even smaller for use in the smaller coronary arteries.

The same types of fluids may be used as in the catheter 100.

The inner tube 222 is disposed within the interior of the dual balloon 234 and within the interior of the guide catheter 202. The inner tube 222 includes a supply lumen 220 and a return lumen 218.

A set of radio opaque marker bands 212 may be disposed on the inner tube 222 for the same reasons disclosed above in connection with the marker bands 112.

As noted above, the proximal portion of the outer balloon 204 is mounted on the outer tube 203 at its distal end. The distal end of the outer balloon 204 is secured to the distal end of the catheter 200 and along the inner tube 222. In contrast, both the proximal and distal ends of the inner balloon 208 may be secured to the inner tube 222 to create a sealed second interior volume 210.

At least two skives 224 and 226 may be defined by the inner tube 222 and employed to allow the working fluid to exit into the second interior volume 210 and to exhaust the same from the second interior volume 210.

A plurality of optional tabs 219 may be employed to roughly or substantially center the inner tube 222 within the catheter 200 as in catheter 100. These tabs may have the same general geometry and design as tabs 119. Of course, they may also be appropriately smaller to accommodate the smaller dimensions of this coronary artery design.

The tabs 119 and 219 are particularly important in the catheters 100 and 200, as contact by the inner tube of the outer tube may also be associated with an undesired conductive heat transfer prior to the working fluid reaching the working region, thereby deleteriously increasing the temperature of the working fluid at the working region.

The method of use of the catheter 200 is generally the same as for the catheter 100. Known techniques may be employed to place the catheter 200 into an affected coronary artery. For the catheter 200, an external guidewire may be used with appropriate attachments to the catheter.

Figure 3:
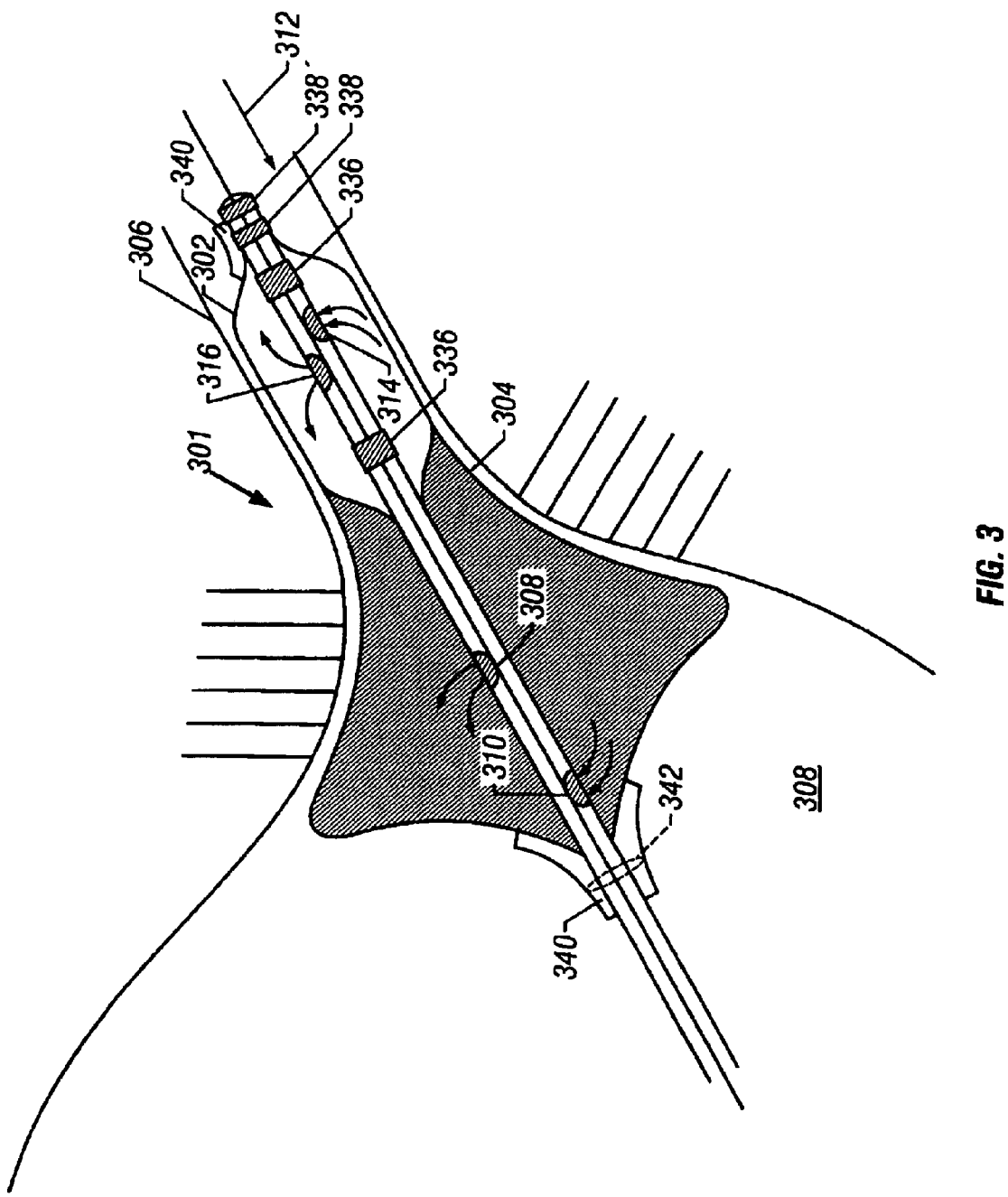
FIG. 3 shows a schematic view of a catheter in use according to a third embodiment of the invention.

Referring to FIG. 3, an alternative embodiment of a catheter 300 which may be employed in PV ablation is detailed. In this figure, a dual balloon system 301 is shown; however, the balloons are not one within the other as in FIG. 1. In this embodiment, a warm balloon 302 is distal of a cold balloon 304. Warm balloon 302 may be used to anchor the system 301 against movements, which may be particularly useful within a beating heart. Cold balloon 304 may then be employed to cryo-ablate a circumferential lesion at the point where a pulmonary vein 306 enters the left atrium 308.

Within the cold balloon 304, a working fluid may be introduced via an outlet port 308 and may be retrieved via an inlet port 310. Ports 308 and 310 may be skived in known fashion into the catheter shaft lumens whose design is exemplified below.

As noted above, the warm balloon 302 serves to anchor the system 301 in the pulmonary vein and left atrium. The warm balloon 302 also serves to stop blood, which is traveling in the direction indicated by arrow 312, from freezing upon contact with the cold balloon 304. In this way, the warm balloon 302 acts as an insulator to cold balloon 304.

As the warm balloon 302 does not require convective heat transfer via a circulating working fluid, it may be served by only one skived port, or by two ports, such as an inlet port 314 and an outlet port 316, as shown in FIG. 3. In some embodiments, a separate lumen or lumens may be used to fill the warm balloon. In an alternative embodiment, a valve mechanism may be used to fill the warm balloon using fluid from the cold balloon. In the case where only one port is used to fill the warm balloon, draining the same requires a slight vacuum or negative pressure to be placed on the lumen servicing the inlet/outlet port. A benefit to the two lumen design is that the warm balloon may be inflated and deflated in a more expeditious manner.

Typical pressures within the warm balloon may be about 1–2 atm (10–30 psi), and thus maintains a fairly low pressure. An appropriate fluid will be biocompatible, and may be Galden fluid, D5W, and so on. Typical pressures within the cold balloon may be about 5–7 atm, for example about 6 atm (e.g., at about 100 psi), and thus maintains a higher pressure. An appropriate fluid may be Galden fluid, e.g., HT-55, D5W, and so on. The volume of fluid required to fill the cold balloon may vary, but may be about 4–8 cc. The cold balloon may be about 2 to 2½ cm long, and have a diameter of 1 to 2½ cm.

In some embodiments, the warm balloon may be glued or otherwise attached to the cold balloon. In the case where only one port is used to fill the warm balloon, draining both balloons may simply entail closing either the return lumen or the supply lumen, and drawing a vacuum on the other. In this way, both the cold and warm balloons may be evacuated. In any case, a standard medical "indeflator" may be used to pressurize and de-pressurize the various lumens and balloons.

Figure 4:
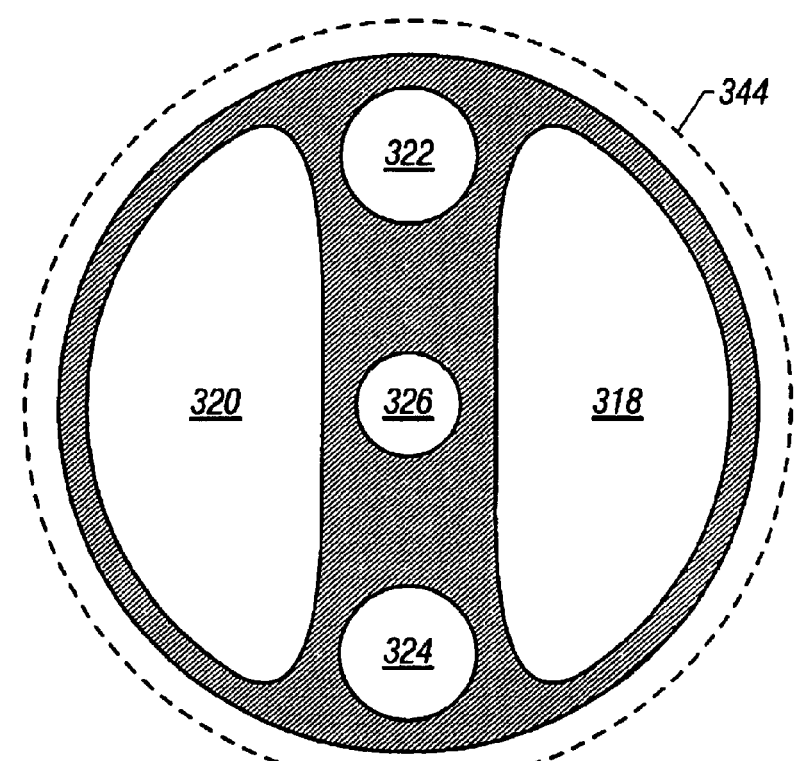
FIG. 4 shows a cross-sectional view of the catheter of FIG. 3.
Figure 5:
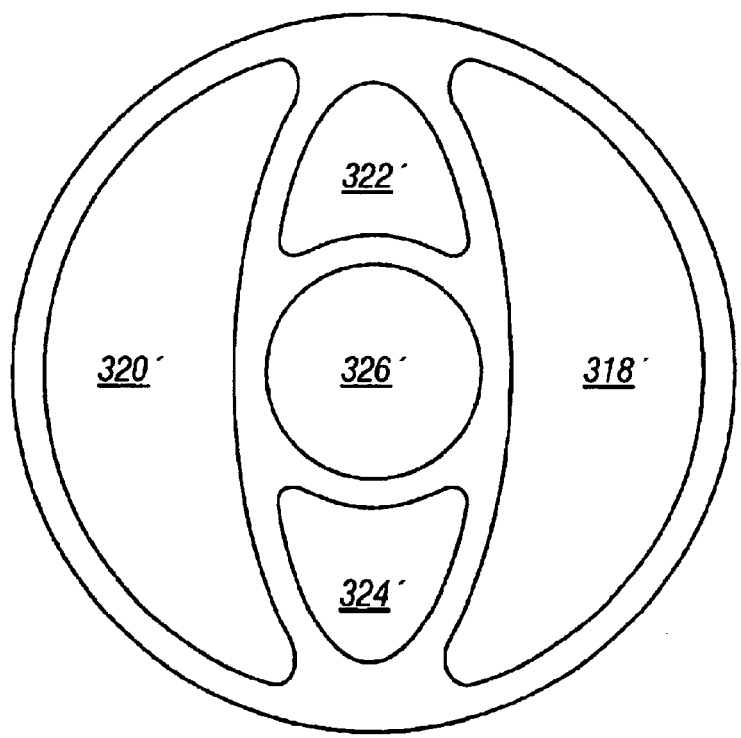
FIG. 5 shows an alternative cross-sectional view of the catheter of FIG. 3.

FIG. 4 shows an embodiment of the arrangement of lumens within the catheter. In particular, supply and return lumens for the cold balloon 304 are shown by lumens 318 and 320, respectively. Supply and return lumens for the warm balloon 302 are shown by lumens 322 and 324, respectively, although as noted only one may be used as required by the dictates of the user. A guidewire lumen 326 is also shown. An alternative arrangement is shown in FIG. 5, where the corresponding lumens are shown by primes.

Figure 6:
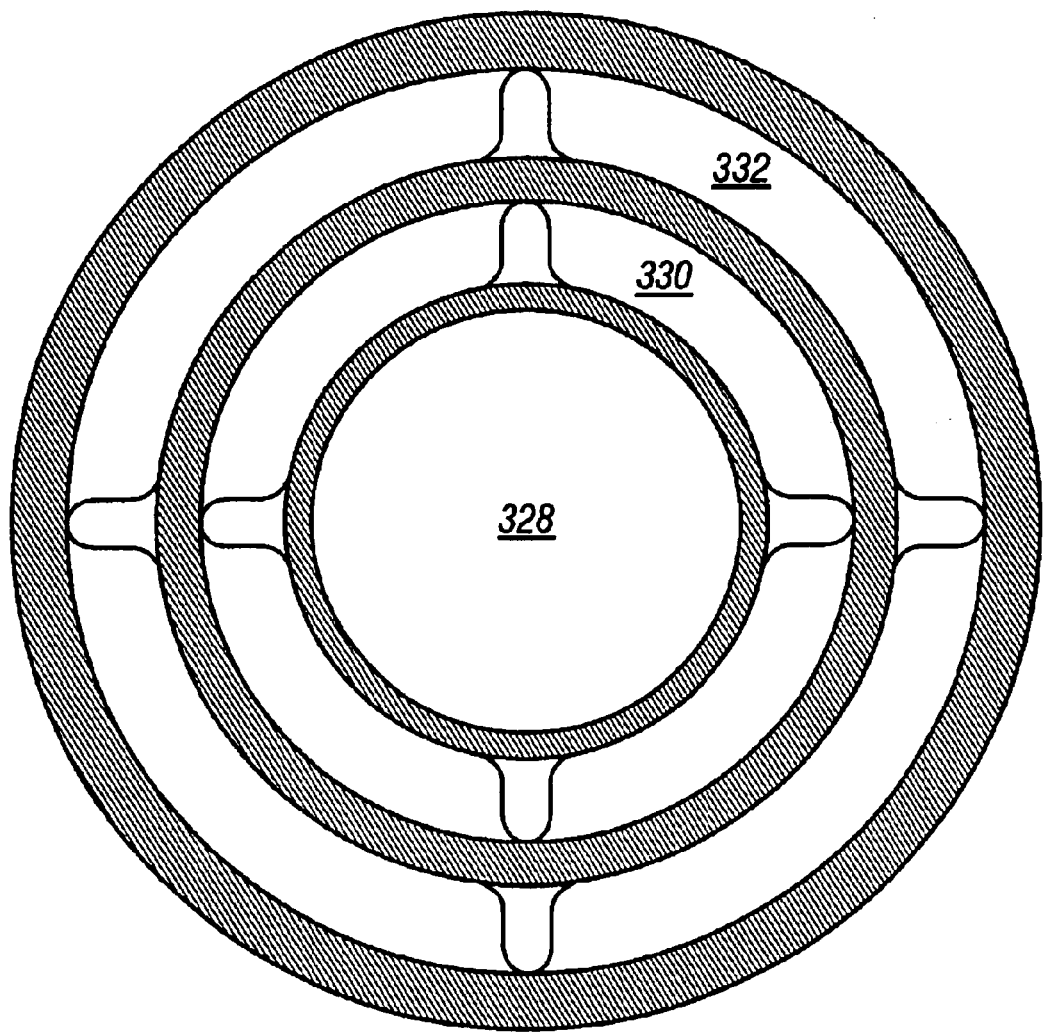
FIG. 6 shows an alternative cross-sectional view of the catheter of FIG. 3.

In the above lumen designs, the exterior blood is exposed to the cold supply flow. Referring to FIG. 6, an alternative lumen design is shown in which the cold fluid supply lumen 328 is exposed to only the cold fluid return lumen 330. An insulation space 332 may also be employed. In this way, the heat flux from the exterior flow is minimized and the cold fluid may reach the cold balloon at a lower temperature. One drawback to such a system is that the operational pressure may be higher.

Referring back to FIG. 4, the overall catheter outer diameter may be about 0.130", e.g. about 10 French, including an insulation sleeve and guide discussed below. The catheter shaft 303 itself may be about 0.110" and may be made of, e.g., polyethylene (PE), and preferably a combination of a low density PE and a high density PE.

Figure 7:
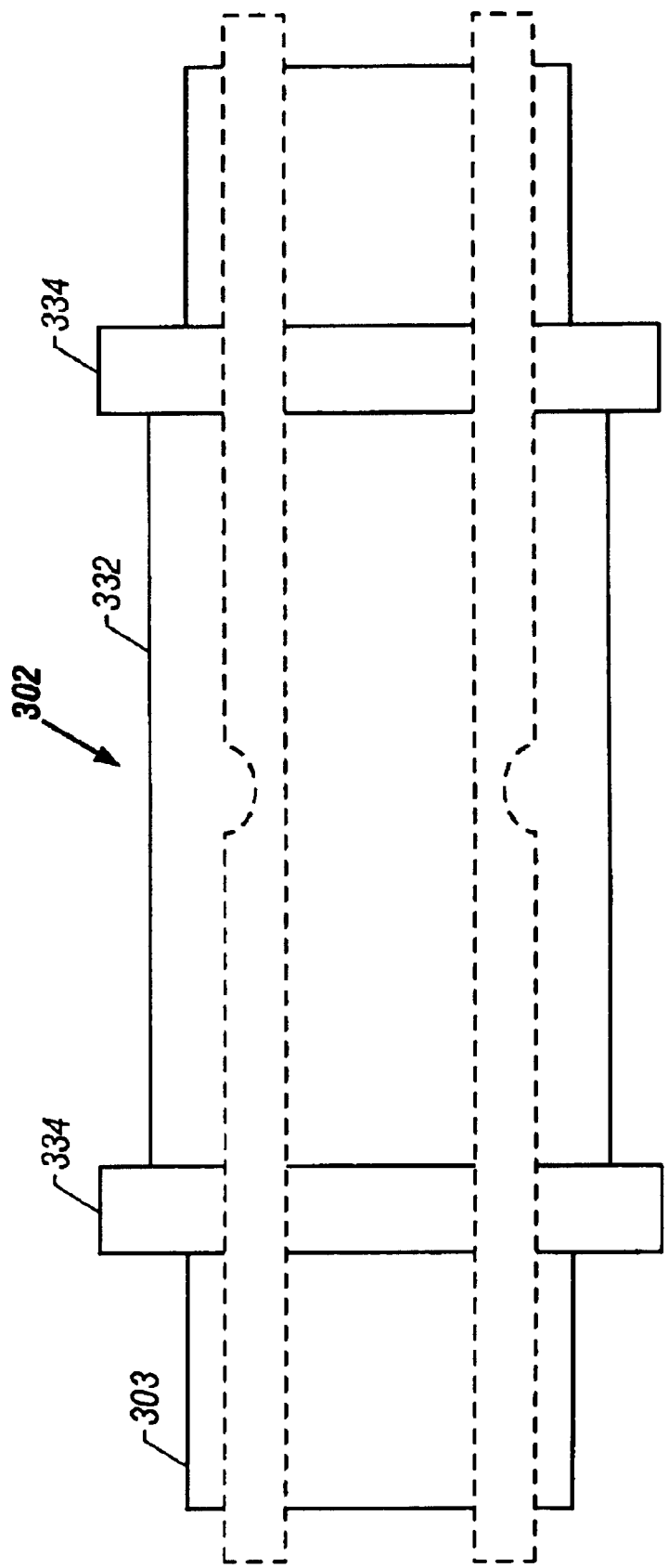
FIG. 7 shows a schematic view of the warm balloon of the catheter of FIG. 3.

The inlet and outlet ports or inlet/outlet port of the warm balloon may be skived from the lumens 322 and 324. Referring to FIG. 7, the warm balloon 302 itself may be made of a sleeve 332 of silicone tubing of, e.g., 35 durometer on the "D" scale, and held in place by two pieces of PET heat shrink tubing 334. Alternative methods of securing the warm balloon during inflation may include metal bands or an adhesive.

Referring back to FIG. 3, marker bands 336 may be employed within either or both of the cold balloon and warm balloon to assist the physician is disposing the same in an appropriate location. The marker bands typically denote the working areas of the balloons, and may be made of Pt, Iridium, Au, etc.

In the ablation procedure, the working cold fluid may exit the circulation system or chiller at, e.g., about −85° C. The circulation system or chiller may be, e.g., a two-stage heat exchanger. The fluid may then enter the catheter at about −70° C. to about −75° C., and may strike the balloon at about −55° C. to about −65° C. The overall procedure may take less than a minute to circumferentially ablate the desired tissue up to several minutes. Of course, these numbers are only exemplary and the same depend on the design of the system and fluids used.

Mapping electrodes 338 may be employed at the distal end of the warm balloon. These mapping electrodes may each have a wire attached, the wires extending down, e.g., the supply and return lumens for the warm fluid or the cold fluid. The mapping electrodes 338 may be used to detect stray electrical fields to determine where ablation may be needed and/or whether the ablation procedure was successful. The mapping electrodes may typically be about 2–3 mm apart from each other.

Construction of the warm balloon typically involves adhering the same to the shaft 303 and skiving the inlet and outlet ports. In some instances, it may be desired to place a silicone sleeve 340 on the proximal and/or distal ends of the warm and/or cold balloons. The silicone sleeve 340 may then serve to further insulate the non-working sections of the balloons from blood that would otherwise potentially freeze during a procedure. The silicone sleeve would typically be attached only at a portion of its length, such as that indicated by circle 342, so that the same may slide along the balloon as the balloon is inflated. In addition to insulation effects, the silicone sleeve also serves to assist in collapsing the balloon during deflation.

The entire catheter shaft 303 may be surrounded by an insulation catheter sleeve 344 (see FIG. 4). Sleeve 344 may have a thickness of, e.g., 0.01 inches, and may be made of a foamed extrusion, e.g., that with voids of air disposed within. The voids further assist the insulating effect since their heat transfer is extremely low. A void to polymer ratio of, e.g., 20% to 30% may be particularly appropriate. Such foamed extrusions are available from, e.g., Applied Medical Resources in Laguna Niguel, Calif., or Extrusioneering, Inc., in Temecula, Calif.

To prevent damage to tissue other than where the ablation is to occur, such as at the insertion site near the femoral vein and around the puncture point through the atrial septum, an insulation sleeve may be used as noted above.

Of course, in certain situations, the warm balloon may be omitted, and only the therapeutic cold balloon used. In a particularly simple system, the therapeutic cold balloon may be employed as a single balloon system without the use of tabs. Such a system may be particularly convenient to manufacture and install.

Figure 8:
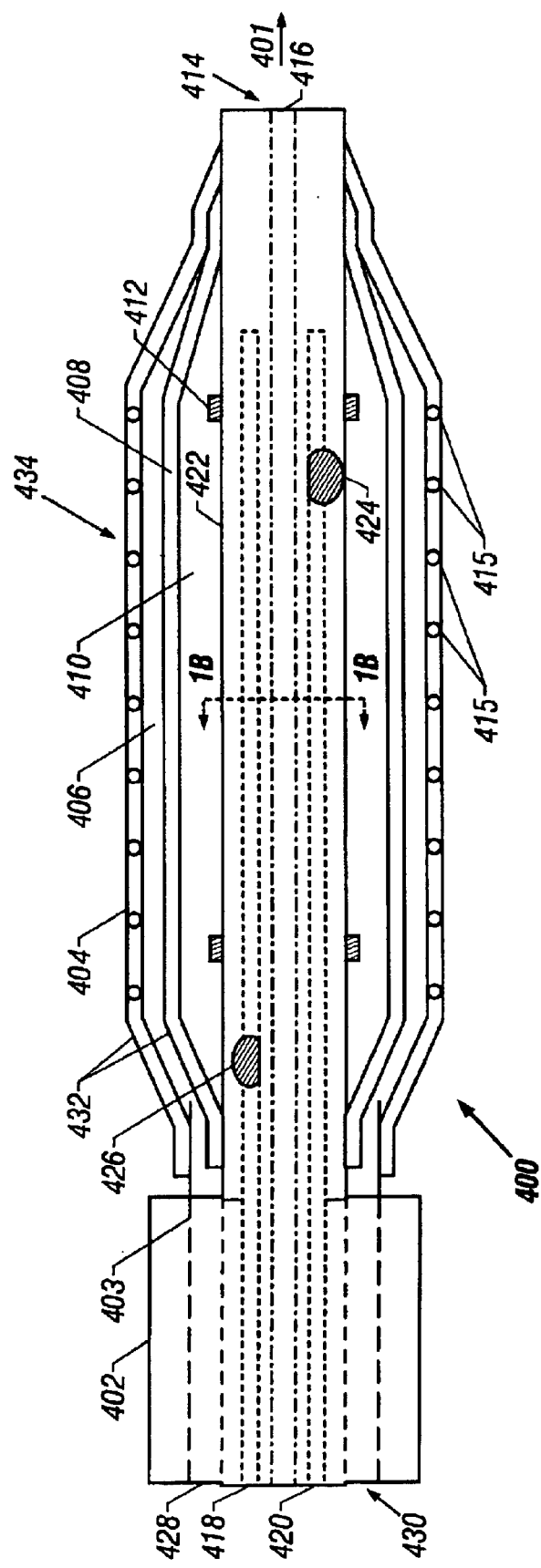
FIG. 8 shows a side schematic view of a catheter according to a fourth embodiment of the invention, this embodiment employing a porous balloon.

In another embodiment, the invention may employ a porous or microporous balloon to enhance heat transfer between the working fluid and the tissue to be treated. Referring to FIG. 8, a catheter 400 is shown according to a first embodiment of the invention. The catheter 400 has a proximal end 430 and a distal end 414. The catheter 400 may be used within a guide catheter 402, and generally includes an outer tube 403, a dual balloon 434, and an inner tube 422. These parts will be discussed in turn.

The guide catheter 402 may be similar to that discussed above in connection with FIG. 1.

The outer tube 403 houses the catheter 400 while the latter traverses the length of the guide catheter 402. The outer tube 403 may have a diameter of about 4 French to 7 French, and the same may be made of polyether blockamide, polybutylene terephtalate, polyurethane, polyamide, polyacetal polysulfone, polyethylene, ethylene tetrafluoroethylene, and other similar materials.

The distal end of the outer tube 403 adjoins the proximal end of the dual balloon 434. The outer tube 403 provides a convenient location for mounting a proximal end of an outer balloon 404 within the dual balloon 434, and further may provide an inlet 428 for providing a fluid such as a liquid to a first interior volume 406 between the dual balloons. In some cases, an inlet 428 per se may not be necessary: the fluid, which may also be a sub-atmospheric level of gas or air, may be provided during manufacture in the first interior volume 406. In this case, the proximal and distal ends of the first interior volume may be sealed during manufacture. The pressure of inflation would then provide the force necessary to cause the fluid within the first interior volume to at least partially "leak" to the tissue. The inlet 428 may be at least partially defined by the annular volume between the interior of the outer tube 403 and the exterior of the inner tube 422.

The dual balloon 434 includes an outer balloon 404 and an inner balloon 408. Between the two is the first interior volume 406. The outer balloon 404 may be inflated by inflating the interior volume 406. The inner balloon 408 has a second interior volume 410 associated with the same. The inner balloon 408 may be inflated by inflating the second interior volume 410.

To avoid the occurrence of bubbles in the bloodstream, both the inner balloon 408 and the outer balloon 404 may be inflated using biocompatible liquids, such as Galden® fluid, perfluorocarbon-based liquids, or various contrast agents. There is no need that the fluid inflating one of the interior volumes be the same fluid as that inflating the other. Additional details on these fluids were described above.

In the case of the first interior volume 406, this fluid may be, e.g., stationary or static: in other words, it need not be circulated. In the case of the second interior volume 410, this fluid would in general be circulated by an external chiller (not shown). The chiller may be, e.g., a gear pump, peristaltic pump, etc. It may be preferable to use a gear pump over a peristaltic pump for the reasons described above.

The inner tube 422 is disposed within the interior of the dual balloon 434 and within the interior of the guide catheter 402. The inner tube 422 includes a supply lumen 420, a return lumen 418, and a guidewire lumen 416. The guidewire lumen 416 may have sizes of, e.g., 17 or 21 mils inner diameter, in order to accommodate current standard sized guidewires, such as those having an outer diameter of 14 mils. This structure may be preferable as described above. The return lumen 418 may be used to exhaust the circulating liquid from the second interior volume to the external chiller. As may be seen from FIG. 8, both lumens 418 and 420 may terminate prior to the distal end 414 of the catheter 400. The lumen arrangement may be similar to that of FIG. 1B or 1C.

A set of radio opaque marker bands 412 may be disposed on the inner tube 422 at locations substantially adjacent the cones 432 to define a central portion of the "working region" of the balloons 404 and 408.

As noted above, the proximal portion of the outer balloon 404 is mounted on the outer tube 403 at its distal end. The distal end of the outer balloon 404 is secured to the distal end of the catheter 400 and along the inner tube 422. In contrast, both the proximal and distal ends of the inner balloon 408 may be secured to the inner tube 422 to create a sealed second interior volume 410.

At least two skives 424 and 426 may be defined by the inner tube 422 and employed to allow the working fluid to exit into the second interior volume 410 and to exhaust the same from the second interior volume. As shown in the figure, the skive 424 is in fluid communication with the lumen 420 and the skive 426 is in fluid communication with the lumen 418. Here, "fluid communication" refers to a relationship between two vessels where a fluid pressure may cause a net amount of fluid to flow from one vessel to the other.

The skives may be formed by known techniques. A suitable size for the skives may be from about 50 mils to 125 mils.

At least one pore 415 may be provided within the outer balloon 404. In this way, a portion of the fluid within the first interior volume 406 may leak to the exterior of the outer balloon 404, contacting the tissue and providing enhanced heat transfer, due to conduction, between the fluid and the tissue to be treated.

The method of making a porous or microporous balloon is known, and either may be employed in this application. Such balloons are alternatively known as "weeping" balloons. In such balloons, pore sizes can be controlled at least to the micron range. The pore size determines the rate of release of the fluid. A conflicting requirement is that the balloon must be inflated and deployed, this requirement having the effect that the balloon must be strong and at least about 1–2 atmospheres of pressure must be maintained in the balloon.

These requirements can still be met in the present porous or microporous balloon as the fluid leakage is generally small, especially as the time of therapy may be on the order of 1–2 consecutive treatments at 60–90 seconds each. Over such a period of time, it may be expected that only 1–2 ml may be leaked.

In alternative embodiments, the pores can be designed to be placed in a band, so as to only leak at about where the circumferential region of tissue is located. Alternatively, the pores can be placed in a helix, spiral, e.g., relative to an axis 401 of the catheter, or other such shape as dictated by the demands of the user. Only one pore may be used in applications where only a minimum of enhanced conductivity is required.

In a treatment-of-restenosis method of use, the guide catheter 402 may be inserted into an affected artery or vein such that the distal tip of the guide catheter is just proximal to an affected area such as a calcified area or lesion.

The catheter 400 may then be inserted over the guide wire via the lumen 416 and through the guide catheter 402. In general, both a guide wire and a guide catheter are not strictly necessary—one or the other may often suffice. During insertion, the dual balloon 434 may be uninflated to maintain a minimum profile. In fact, a slight vacuum may be drawn to further decrease the size of the dual balloon 434 so long as the structural integrity of the dual balloon 434 is not thereby compromised.

The fine positioning step by way of the radio opaque marker bands 412 and as described above in connection with FIG. 1 may then occur. Once placed, a biocompatible heat transfer fluid, which may also contain contrast media, may be infused into the first interior volume 406 through the inlet 428. This fluid then begins to leak via pores 415, flowing between the balloon and the tissue to be treated and enhancing the conductive heat transfer between the two.

The biocompatible cooling fluid may then be circulated through the supply lumen 420 and the return lumen 418. As noted above in connection with FIG. 1, the fluid exits the supply lumen 420 through the skive 424 and returns to the chiller through the skive 426 and via the return lumen 418. It is understood again that the respective skive functions may also be reversed without departing from the scope and spirit of the invention.

Upon completion of the therapy, the circulation of the biocompatible cooling fluid may cease. The remaining heat transfer fluid within the first interior volume 406 may be withdrawn though the inlet 428. The balloons 404 and 408 may be collapsed by pulling a soft vacuum through any or all of the lumens 424, 426, and 428. Following collapse, the catheter 400 may be withdrawn from the treatment site and from the patient through the guide catheter 402.

Figure 9:
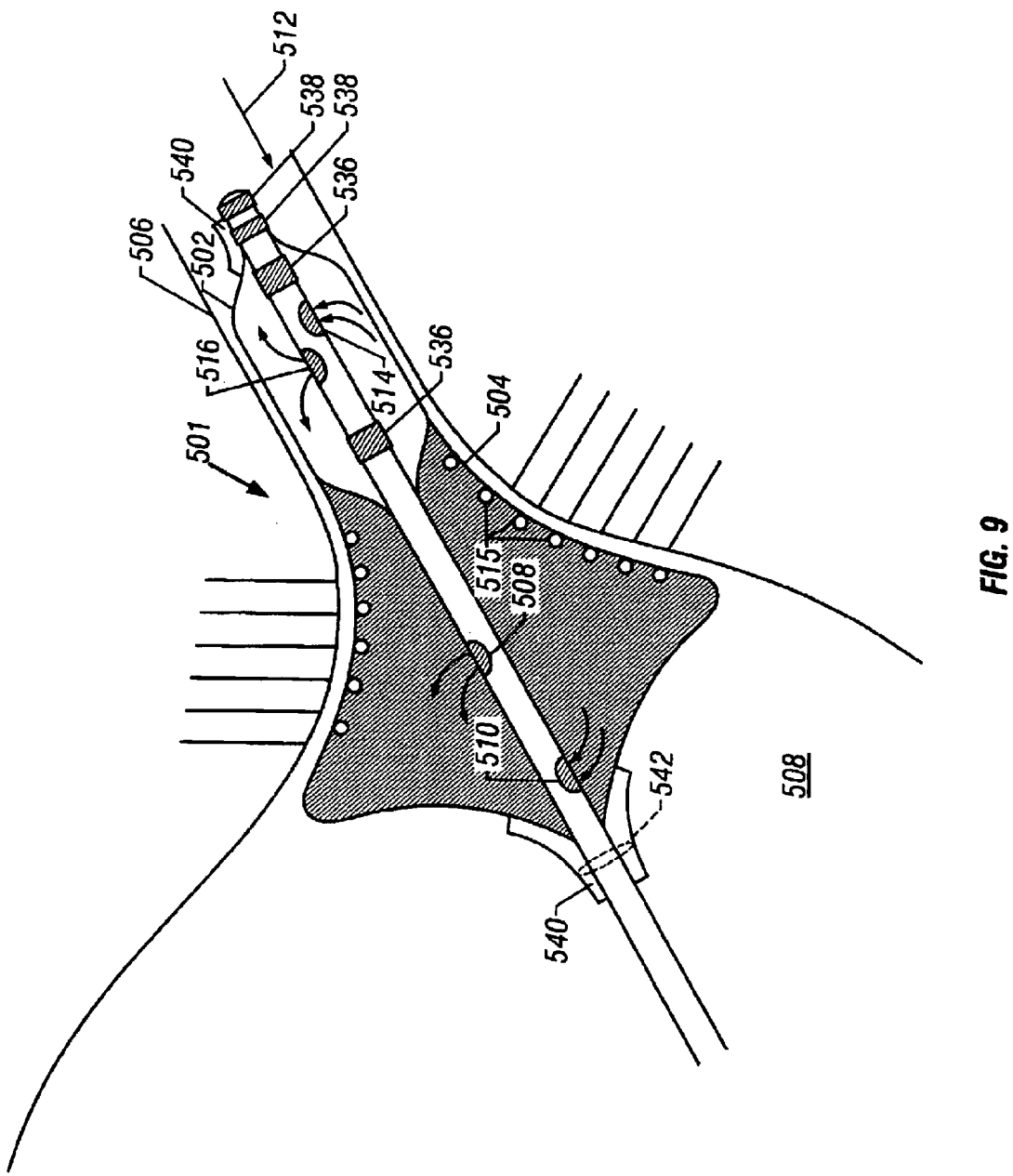
FIG. 9 shows a side schematic view of a catheter according to a fifth embodiment of the invention, this embodiment employing a porous balloon.

Referring to FIG. 9, an alternative embodiment of a catheter which may be employed in PV ablation is detailed. In this figure, a dual balloon system 501 is shown which is similar to the embodiment of FIG. 3.

However, the balloons are not one within the other as in FIG. 1. In this embodiment, warm balloon 502 may be used to anchor the system 501 against movements, while cold balloon 504 may be employed to cryo-ablate a circumferential lesion at the point where a pulmonary vein 506 enters the left atrium 508.

Within the cold balloon 504, a working fluid may be introduced via an outlet port 508 and may be retrieved via an inlet port 510. Ports 508 and 510 may be skived in known fashion into the catheter shaft lumens whose design is exemplified below. The cold balloon 504 may be a porous or microporous balloon, having pores as indicated in FIG. 9 by pores 515.

As in the embodiment of FIG. 3 noted above, the warm balloon 502 serves to anchor the system 501 in the pulmonary vein and left atrium. The warm balloon 502 also serves to stop blood, which is traveling in the direction indicated by arrow 512, from freezing upon contact with the cold balloon 504. In this way, the warm balloon 502 acts as an insulator to cold balloon 504.

As the warm balloon 502 does not require convective heat transfer via a circulating working fluid, it may be served by only one skived port, or by two ports, such as an inlet port 514 and an outlet port 516, as shown in FIG. 9. In some embodiments, a separate lumen or lumens may be used to fill the warm balloon. In an alternative embodiment, a valve mechanism may be used to fill the warm balloon using fluid from the cold balloon. In the case where only one port is used to fill the warm balloon, draining the same requires a slight vacuum or negative pressure to be placed on the lumen servicing the inlet/outlet port.

Typical pressures within the warm balloon may be as above. Typical pressures within the porous cold balloon may be about 1–2 atm, for example about 1.5 atm. An appropriate cryogenic fluid may be Galden fluid, e.g., HT-55, or others with similar properties. The volume of fluid required to fill the cold balloon may vary, but may be about 4–8 cc. The cold balloon may be about 2 to 2½ cm long, and have a diameter of 1 to 4 cm.

A porous or microporous balloon may also be employed in an application in which the above or similar balloons are employed to treat restenosis. For example, following an angioplasty procedure, the angioplasty balloon may be removed while the guidewire left in place. As with treatment-of-atrial fibrillation procedures, the balloon may be delivered up to the location of treatment via the guidewire, and operated for a minute, or other appropriate time as determined by, e.g., the physician. In the restenosis application, the outer diameter of the catheter would typically be less than about 6 French, as the same would require compatibility with existing coronary angioplasty hardware, such as a 9 French guide catheter.

Figure 15:
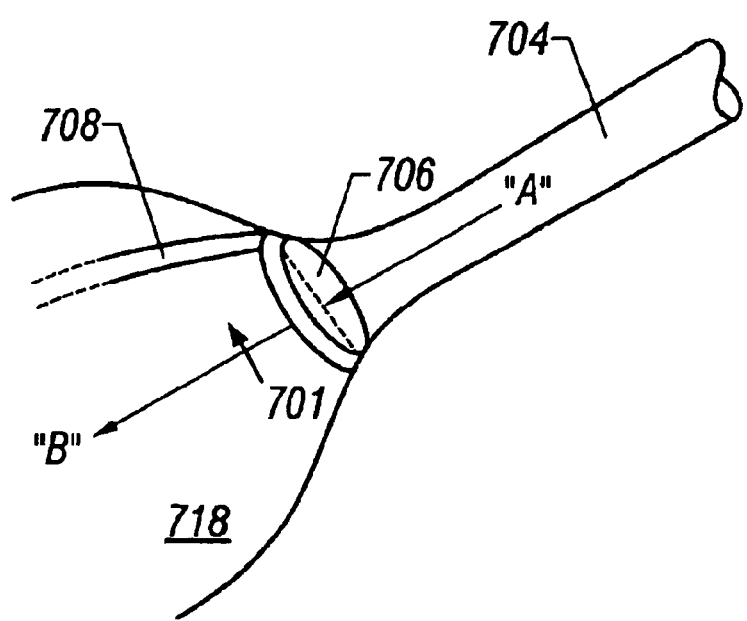
FIG. 15 shows an embodiment of a device that may be employed in the present invention to perform cryoablation while allowing blood flow during an ablation procedure.
Figure 16:
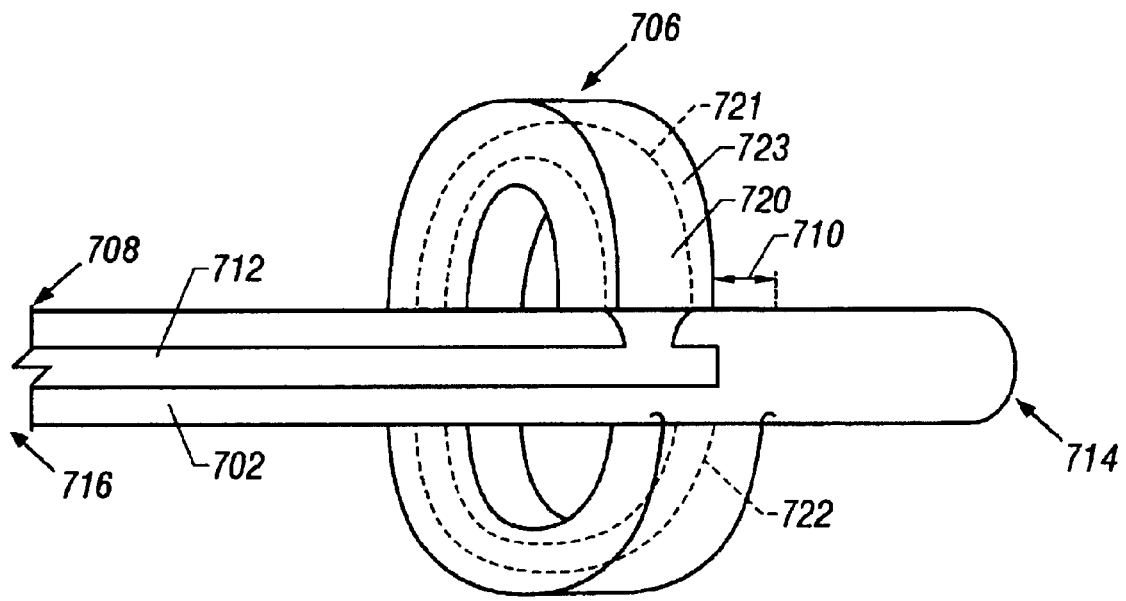
FIGS. 16 and 17 show more detailed views of the embodiment of FIG. 15.

In another embodiment, referring to FIGS. 15 and 16, a device 701 is shown which may be employed for treatment of atrial fibrillation by circumferential ablation, while allowing blood flow to continue, thereby reducing, minimizing, or eliminating the risk of stroke during long cryoablation procedures. Referring to the figures, an annular ring balloon 706 having a toroidal shape is fluidically coupled to a catheter shaft 708 near the distal end 714 thereof. The annular ring balloon 706 may be inflated by any of the various fluids described elsewhere in this specification, and may further cause the cryoablation of a circumferential region of tissue at a location where the pulmonary vein 704 meets the left atrium 718, i.e., the ostium of the pulmonary vein. Blood flow is then only minimally impeded as the same flows between location A and location B. The diameter of the interior annulus may be appropriately sized to accomplish this objective.

A more detailed view is shown in FIG. 16. In this figure, a supply lumen 712, also termed a catheter supply lumen, provides the cryoablation fluid to an interior of the annular ring balloon 706 to inflate the same. A roughly annular portion 702 of the shaft 708 surrounding the supply lumen 712 serves as a catheter return lumen for return of the cryoablation fluid to exhaust the balloon.

A portion of the annular ring balloon 706 adjacent the supply lumen is denoted fluid inlet 720, while a portion of the annular ring balloon 706 adjacent the return lumen is denoted fluid outlet 722. Fluid inlet 720 may be offset, in the direction of the axis of shaft 708, from fluid outlet 722. For example, the fluid inlet 720 may be slightly proximal of the fluid outlet 722. This accomplishes a greater ease in trackability of the uninflated device, as well as more convenient manufacturability.

The radius of expansion should be sufficient to enable overlap 710 at the point where the balloon is coupled to the shaft, so as to ensure a contiguous cryo-ablation injury, but not so great as to impede the blood flow. A view even better showing this is shown in FIG. 17.

Figure 17:
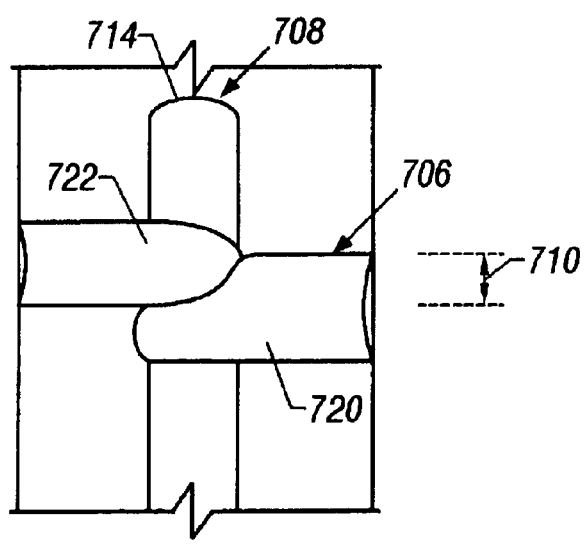

The above device of FIGS. 15–17 may further be employed for angioplasty procedures, as will be realized given the teaching above.

The annular ring balloon may be manufactured in a way similar to current balloons. It may be a basic cylinder with tapered ends that mate with the catheter shaft. The plane of the balloon is normal to the catheter shaft. This concept is different from centering balloons in a number of ways, which typically are designed to enable blood flow between the vascular wall and the balloon. It may also be distinct from coronary perfusion catheters that are designed to re-route blood flow through the catheter shaft. The outer diameter of the toroidal annular ring balloon may be about 1 cm.

While the description with respect to FIGS. 15–17 has been described such that the supply lumen only extends to a fluid inlet of the annular ring balloon, in another embodiment, the supply lumen extends throughout the annular ring balloon. This is then termed a balloon supply lumen and the same is indicated in FIG. 16 by dotted lines showing balloon supply lumen 721 and balloon return lumen 723. In this way, the annular ring balloon itself is biaxial, having a balloon supply and balloon return lumen within. In this case, the balloon return lumen, which is generally warmer, may be disposed towards the inner radius of the balloon, adjacent to which the blood is flowing. Correspondingly, the balloon supply lumen may be disposed towards the outer radius of the balloon, where the cryo-ablation is to occur.

Whether the application is for restenosis or for treatment of atrial fibrillation, it is noted that on occasion tissue may be thermally damaged unintentionally. For example, at the point where catheter tubing enters the patient, relatively constant contact of the tubing with the tissue may lead to thermal damage. The same may be true at the point where tubing penetrates the atrial septum, in atrial fibrillation situations. To treat such situations, one or a combination of the below embodiments may be employed. In these embodiments, insulating or warming the affected regions is performed via modifying a portion or more of the full-length introducer or sheath that houses the catheter from the site of insertion into the left atrium.

Figure 10:
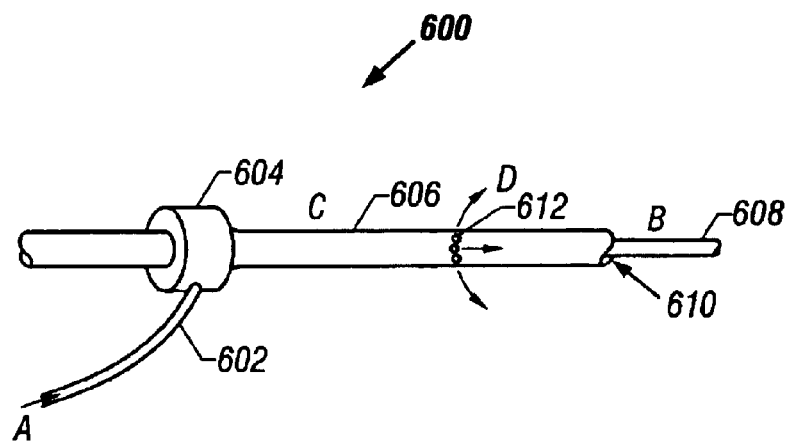
FIG. 10 shows a first embodiment of a device that may be employed in the present invention to prevent tissue damage at, e.g., the point of catheter insertion into the patient's body.

Referring to FIG. 10, an embodiment of an introducer sheath 600 is shown that prevents freezing around the site of the percutaneous insertion. Introducer or introducer sheath 600 generally has an introducer tube 606 at a distal end and a hub 604 at a proximal end. A catheter 608 for cryoablation may be seen in schematic form emerging from the distal end of the introducer tube 606. Warmed fluid, such as injection grade saline, is introduced via an optional insertion tube 602 to the hub 604. This fluid traverses the annular region 610 between an exterior wall of the catheter shaft 608 and an interior wall of the introducer tube 606. The fluid loses heat to the catheter, becoming cooled in the process, and exits the interior of the introducer of sheath 600 via outlet ports 612. These outlet ports are positioned on the introducer is such a way as to exhaust the cooled fluid directly into venous blood. Forced convection of the fluid between the catheter shaft and the introducer prevents the temperature on the exterior of the introducer from falling to dangerous levels, such as near freezing.

In a second embodiment, a resistive heater may be employed. In particular, referring to FIG. 11, an embodiment of an introducer or sheath 600' is shown that prevents freezing around the site of the percutaneous insertion. Introducer or sheath 600' generally has an introducer tube 606' at a distal end and a hub 604' at a proximal end. A catheter 608 for cryoablation may be seen in schematic form emerging from the distal end of the introducer tube 606'. A resistive heater 614 is wound around the introducer tube 606' and is conductively coupled to wires 616 leading to control unit 618. The heater 614 may be in the form of a helical wire or strip, applied to the exterior of the introducer tube 606', and of sufficient length so as to extend into the accessed vein. The heater may be characterized in such a way that the resistance is a function of temperature.

An external power source and control unit 618 may be employed to maintain the temperature of the heating coil 614 at the desired value, preferably nominal body temperature (37° C.), thus preventing thermal damage to adjacent tissue. Of course, the external power source and control unit may be within one or two or more separate physical units.

The helical form of coil 614 may be preferred; however, various other geometries of resistive heaters may also be used.

Figure 11:
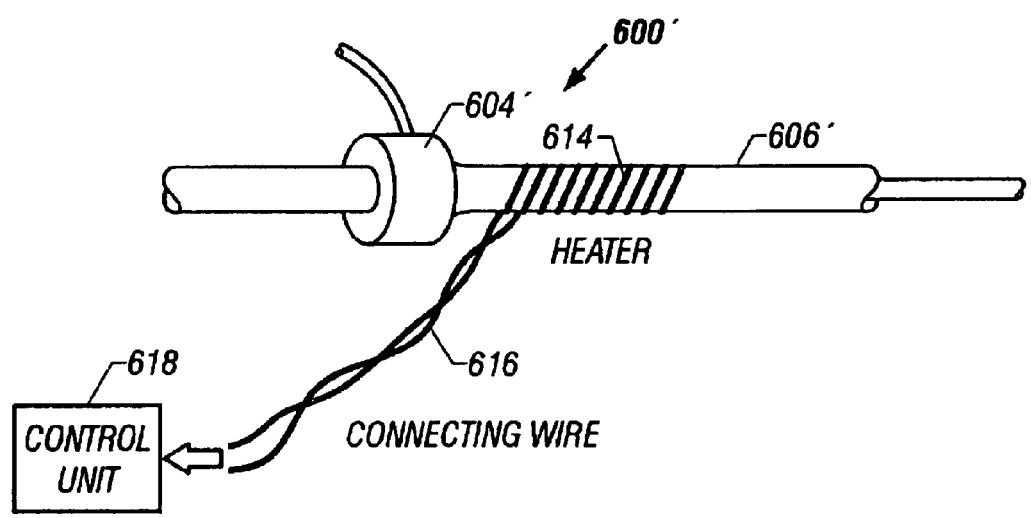
FIG. 11 shows a second embodiment of a device that may be employed in the present invention to prevent tissue damage at, e.g., the point of catheter insertion into the patient's body.
Figure 12:
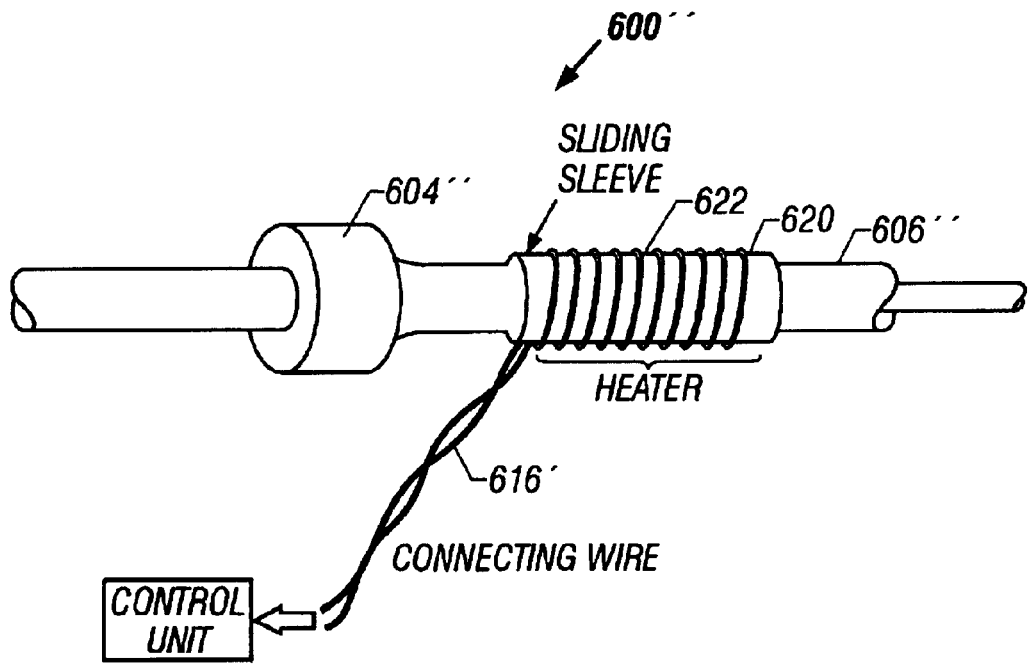
FIG. 12 shows a third embodiment of a device that may be employed in the present invention to prevent tissue damage at, e.g., the point of catheter insertion into the patient's body.

In a related embodiment, referring to FIG. 12, another embodiment 600" is shown that prevents freezing of tissue around the site of percutaneous insertion. A resistive heater 622 in the form of a helical wire or strip is applied to the exterior of a sleeve 620 which fits tightly over and yet is free to move on the exterior surface of the introducer 606". When the catheter and introducer are in place, the sleeve 620 is positioned so as to encompass the tissue between the insertion site and the interior of the accessed vein. An external power source and control circuit, which may be similar to that employed in FIG. 11, are employed to maintain the temperature of the heating coil 622 at the desired value, preferably nominal body temperature (37° C.), thus preventing thermal damage to adjacent tissue. As before, the helical form, while preferred, is not the only geometry of resistive heater to which this disclosure may apply.

The location of percutaneous insertion is not the only location at which tissue damage may occur. For example, damage may also occur at the atrial septum or other locations where the device may rest against tissue for periods of time.

Figure 13:
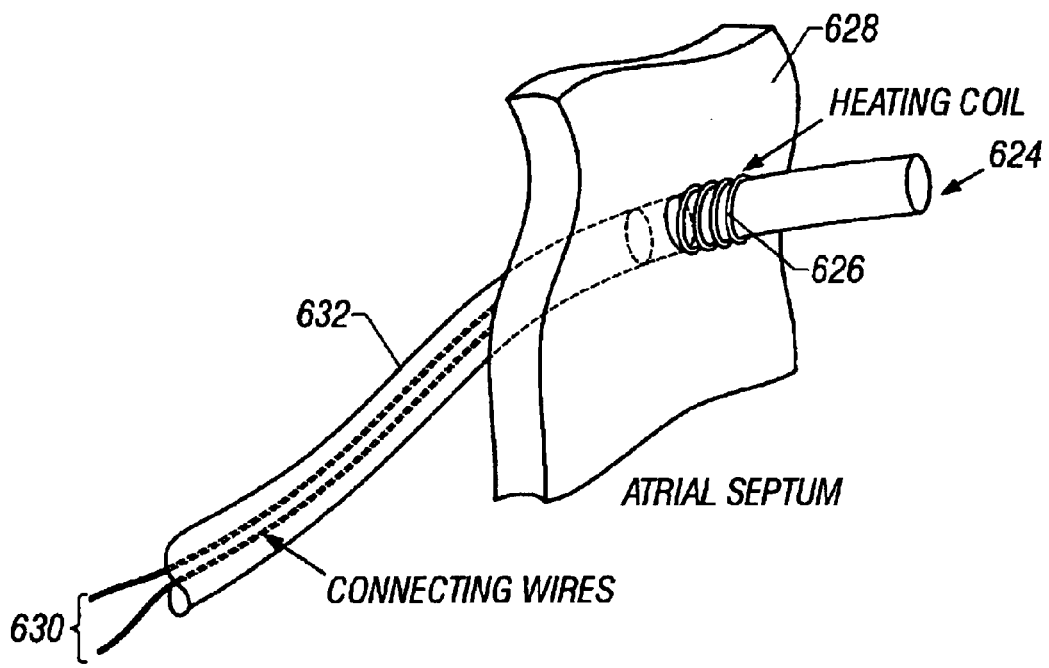
FIG. 13 shows a first embodiment of a device that may be employed in the present invention to prevent tissue damage at, e.g., the atrial septum.

Referring to FIG. 13, an embodiment is shown that prevents freezing of tissue around the site of penetration of the introducer through the atrial septum. A resistive heater 626 in the form of a helical wire or strip is applied to the exterior of the introducer 632 near the distal tip 624, so that the length of the heater 626 encompasses the entire path of the introducer 632 through the atrial septum 628. As noted above, an external power source and control circuit are employed to maintain the temperature of the heating coil at the desired value, preferably nominal body temperature (37° C.), thus preventing thermal damage to adjacent tissue. The helical form, while preferred, is not the only geometry of resistive heater to which this disclosure may apply.

Figure 14:
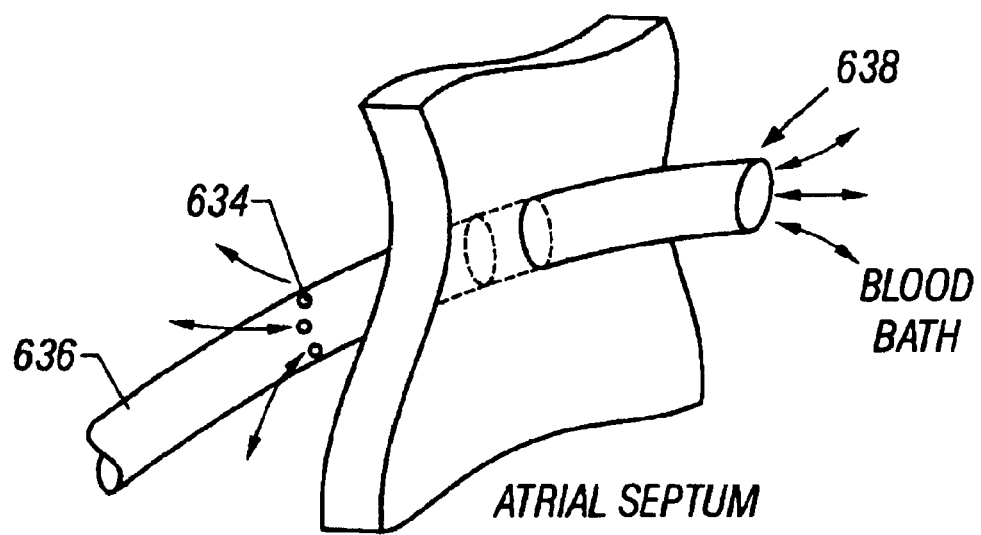
FIG. 14 shows a second embodiment of a device that may be employed in the present invention to prevent tissue damage at, e.g., the atrial septum.

Referring to FIG. 14, another embodiment is shown that prevents freezing of tissue around the site of penetration of the introducer through the atrial septum. Several holes 634 are drilled around the circumference of the introducer 636 proximal to the distal tip 638. These holes 634 are placed so that on proper placement of the introducer 636, a fluid path is created between the right and left atria. This fluid path is along an annular sleeve formed by the interior wall of the introducer and the exterior wall of the catheter. The oscillating pressure gradient between the two atria induces a corresponding flow of blood along the annular path connecting the distal tip of the introducer to the holes on the introducer within the contralateral atrium. Forced convection of blood between the catheter shaft and introducer prevents the temperature on the exterior of the introducer from falling to dangerous levels (near freezing).

In this embodiment, as well as in others, the sheath or introducer serves a number of functions in addition to its role as a guide. For example, it provides another important layer of insulation so that heat from the body does not unduly enter the catheter, unnecessarily heating the working fluid inside prior to the fluid reaching the cryoablation balloon.

The invention has been described above with respect to particular embodiments. It will be clear to one of skill in the art that numerous variations may be made from the above embodiments with departing from the spirit and scope of the invention. For example, the invention may be combined with stent therapies or other such procedures. The dual balloon disclosed may be used after angioplasty or may be an angioplasty balloon itself. Furthermore, while the invention has occasionally been termed herein a "cryoplasty catheter", such a term is for identification purposes only and should not be viewed as limiting of the invention. Fluids that may be used as heat transfer fluids include perfluorocarbon-based liquids, i.e., halogenated hydrocarbons with an ether bond, such as FC 72. Other materials that may be used include CFCs, Freon®, or chemicals that when placed together cause an endothermic reaction. Preferably, low viscosity materials are used as these result generally in a lessened pressure drop. The balloons may be made, e.g., of Pebax, PET/PEN, PE, PA 11/12, PU, or other such materials. Either or both of the dual balloons may be doped to improve their thermal conductivities. The shafts of various tubes mentioned, such as inner tube 122, may be made of Pebax, PBT, PI/PEI, PU, PA 11/12, SI, or other such materials. The precise shapes and dimensions of the inner and outer lumens, while indicated in, e.g., FIGS. 1B, 1C, and 2B, may vary. The lumen design shown in FIGS. 1B–1C may be employed in the catheter of FIG. 2A and vice-versa. Either a single cold balloon system, or a dual balloon system, may be employed in either or both of the mentioned applications of treating restenosis or atrial fibrillation, or other such maladies. Embodiments of the invention may be employed in the field of cold mapping, where a circle of tissue is cooled to see if the affected part has been reached. If the affected tissue is that which is being cooled, a more vigorous cooling may be instituted. Other variations will be clear to one of skill in the art, thus the invention is limited only by the claims appended hereto.

What is claimed is:

1. A device to treat tissue while preventing tissue damage to adjacent tissue, comprising:
    an ablation catheter, wherein the catheter includes:
        a guidewire lumen;
        a supply lumen; and
        a return lumen;
    a tubular introducer sheath for the ablation catheter, wherein said ablation catheter is insert through and extends past a distal end of the introducer sheath, and further wherein, in use, the device is adapted to be positioned such that the ablation catheter contacts tissue to be treated and the introducer sheath contacts tissue to be protected;
    a heater disposed adjacent or within the introducer sheath, the heater thermally coupled to the tissue;
    a source of cryofluid having a supply tube and a return tube, the supply tube coupled in fluid communication to the supply lumen and the return tube coupled in fluid communication to the return lumen; and
    a control unit for the heater.

2. The device of claim 1, wherein the heater is a resistive heater.

3. The device of claim 1, wherein the heater includes an inlet tube fluidically coupled to an interior of the introducer, and at least one outlet orifice disposed in the introducer.

4. The device of claim 1, wherein the heater includes an inlet sleeve with an input for a body fluid at a distal end of the introducer sheath, wherein the inlet sleeve is fluidically coupled to an interior of the introducer, and at least one outlet orifice disposed in the introducer.

5. The device of claim 4, wherein the inlet sleeve has an annular shape along a portion thereof.

6. The device of claim 2, wherein the resistive heater is disposed on a sleeve, the sleeve concentric with the introducer sheath.

7. The device of claim 6, wherein the resistive heater is helically wound on the sleeve.

8. The device of claim 1, wherein the guidewire lumen extends from a proximal end of the ablation catheter to a distal end of the ablation catheter.

9. The device of claim 1, further comprising at least one marker band disposed on the ablation catheter to locate a working region of the device at a desired location.

10. The device of claim 1, wherein the cryofluid is a perfluorocarbon.

11. The device of claim 10, wherein the cryofluid is Galden® fluid.

12. The device of claim 1, wherein the cryofluid is DMSO.

13. The device of claim 1, wherein the cryofluid is D-limonene.

14. The device of claim 1, further comprising a gear pump for circulating the cryofluid.

15. The device of claim 14, wherein the gear pump is one selected from the group consisting of a radial spur gear pump and a helical tooth gear pump.

* * * * *